(12) United States Patent
Amble et al.

(10) Patent No.: US 9,092,556 B2
(45) Date of Patent: *Jul. 28, 2015

(54) MULTI-SITE DATA SHARING PLATFORM

(71) Applicant: eagleyemed, Inc., Santa Clara, CA (US)

(72) Inventors: Ravi N. Amble, San Jose, CA (US); Harish P. Hiriyannaiah, San Jose, CA (US); Farooq Mirza Mohammad Raza, Milpitas, CA (US); Steven J. Salve, San Jose, CA (US)

(73) Assignee: eagleyemed, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/505,367

(22) Filed: Oct. 2, 2014

(65) Prior Publication Data

US 2015/0035959 A1 Feb. 5, 2015

Related U.S. Application Data

(63) Continuation-in-part of application No. 14/292,258, filed on May 30, 2014, which is a continuation-in-part of application No. 14/214,321, filed on Mar. 14, 2014.

(60) Provisional application No. 61/800,316, filed on Mar. 15, 2013, provisional application No. 61/829,905, filed on May 31, 2013.

(51) Int. Cl.
*G06F 11/30* (2006.01)
*G06F 19/00* (2011.01)
(Continued)

(52) U.S. Cl.
CPC .......... *G06F 19/3418* (2013.01); *A61B 5/0006* (2013.01); *A61B 5/0008* (2013.01); *A61B 5/0013* (2013.01); *A61B 5/0022* (2013.01); *A61B 5/0035* (2013.01); *A61B 5/0077* (2013.01); *A61B 5/01* (2013.01); *A61B 5/02055* (2013.01); *A61B 5/0402* (2013.01); *A61B 5/0476* (2013.01); *A61B 5/055* (2013.01); *A61B 5/14532* (2013.01); *A61B 5/14551* (2013.01); *A61B 5/743* (2013.01); *A61B 5/7425* (2013.01); *A61B 5/7475* (2013.01); *A61B 6/032* (2013.01); *A61B 6/468* (2013.01); *A61B 6/5294* (2013.01); *A61B 8/13* (2013.01); *A61B 8/463* (2013.01);
(Continued)

(58) Field of Classification Search
CPC ................................. G06F 21/72; G06F 21/10
USPC .......................................................... 713/189
See application file for complete search history.

(56) References Cited

U.S. PATENT DOCUMENTS 5,441,047 A 8/1995 David et al.
5,553,609 A 9/1996 Chen et al.
(Continued)

OTHER PUBLICATIONS

U.S. Appl. No. 14/292,258, filed May 30, 2014.
(Continued)

*Primary Examiner* — Anthony Brown
(74) *Attorney, Agent, or Firm* — Beyer Law Group LLP

(57) ABSTRACT

A variety of methods and arrangements for sharing medical data are described. In one aspect, one or more data streams are received from one or more medical imaging/sensing or other types of devices. Frames are obtained from the streams. In some embodiments, particular frames and/or parts of frames are selectively encrypted. The frames are transmitted to a remote device, where they are rendered and/or displayed at the remote device. In various embodiments, the frames of different streams are synchronized.

20 Claims, 17 Drawing Sheets

(51) Int. Cl.

| | |
|---|---|
| *H04N 7/18* | (2006.01) |
| *G11B 27/11* | (2006.01) |
| *A61B 5/00* | (2006.01) |
| *A61B 8/13* | (2006.01) |
| *A61B 6/03* | (2006.01) |
| *A61B 6/00* | (2006.01) |
| *A61B 8/00* | (2006.01) |
| *A61B 8/08* | (2006.01) |
| *A61B 5/0402* | (2006.01) |
| *A61B 5/0476* | (2006.01) |
| *A61B 5/1455* | (2006.01) |
| *A61B 5/145* | (2006.01) |
| *A61B 5/0205* | (2006.01) |
| *A61B 5/01* | (2006.01) |
| *A61B 5/055* | (2006.01) |
| *A61B 5/021* | (2006.01) |
| *A61B 5/024* | (2006.01) |
| *A61B 5/08* | (2006.01) |

(52) U.S. Cl.
CPC .............. *A61B 8/468* (2013.01); *A61B 8/5292* (2013.01); *A61B 8/565* (2013.01); *G06F 19/321* (2013.01); *G11B 27/11* (2013.01); *H04N 7/183* (2013.01); *A61B 5/021* (2013.01); *A61B 5/02416* (2013.01); *A61B 5/08* (2013.01)

(56) References Cited

U.S. PATENT DOCUMENTS

| | | | |
|---|---|---|---|
| 5,827,180 | A | 10/1998 | Goodman |
| 5,987,519 | A | 11/1999 | Peifer et al. |
| 6,083,248 | A | 7/2000 | Thompson |
| 6,364,834 | B1 | 4/2002 | Reuss et al. |
| 6,381,577 | B1 | 4/2002 | Brown |
| 6,424,996 | B1 | 7/2002 | Killcommons et al. |
| 6,442,432 | B2 | 8/2002 | Lee |
| 6,599,250 | B2 | 7/2003 | Webb et al. |
| 6,681,003 | B2 | 1/2004 | Linder et al. |
| 6,705,990 | B1 | 3/2004 | Gallant et al. |
| 6,738,798 | B1 | 5/2004 | Ploetz et al. |
| 6,804,656 | B1 | 10/2004 | Rosenfeld et al. |
| 6,820,057 | B1 | 11/2004 | Loch et al. |
| 7,038,588 | B2 | 5/2006 | Boone et al. |
| 7,188,151 | B2 | 3/2007 | Kumar et al. |
| 7,549,961 | B1 | 6/2009 | Hwang |
| 8,005,691 | B2 | 8/2011 | Kumar et al. |
| 8,069,420 | B2 | 11/2011 | Plummer |
| 2001/0056226 | A1 | 12/2001 | Zodnik et al. |
| 2002/0198473 | A1 | 12/2002 | Kumar et al. |
| 2003/0046562 | A1 | 3/2003 | Uchikubo |
| 2004/0039606 | A1 | 2/2004 | Loch et al. |
| 2007/0130287 | A1 | 6/2007 | Kumar et al. |
| 2007/0217501 | A1 | 9/2007 | Siemens et al. |
| 2008/0146277 | A1 | 6/2008 | Anglin et al. |
| 2009/0125147 | A1 | 5/2009 | Wang et al. |
| 2009/0189988 | A1 | 7/2009 | Jia et al. |
| 2009/0192824 | A1 | 7/2009 | Minakuchi et al. |
| 2010/0290683 | A1* | 11/2010 | Demeester et al. ........... 382/131 |
| 2010/0325546 | A1 | 12/2010 | Leo et al. |
| 2011/0134203 | A1 | 6/2011 | Smelyansky et al. |
| 2011/0135149 | A1* | 6/2011 | Gefen ........................... 382/103 |
| 2011/0301461 | A1 | 12/2011 | Anite |
| 2012/0173282 | A1 | 7/2012 | Kelley |
| 2012/0179039 | A1 | 7/2012 | Pellissier et al. |
| 2012/0290976 | A1 | 11/2012 | Lahm et al. |
| 2013/0093829 | A1 | 4/2013 | Rosenblatt et al. |
| 2014/0282018 | A1 | 9/2014 | Amble et al. |

OTHER PUBLICATIONS

International Search Report dated Nov. 24, 2014 from International Application No. PCT/US14/40363.
Written Opinion dated Nov. 24, 2014 from International Application No. PCT/US14/40363.
International Search Report dated Aug. 20, 2014 from International Application No. PCT/US2014/029590.
International Preliminary Examination Report dated Jan. 24, 2003 from PCT Application No. PCT/US02/09914.
Federal Information Processing Standards, "Advanced Encryption Standard (AES", Publication 197, Nov. 26, 2001.

* cited by examiner

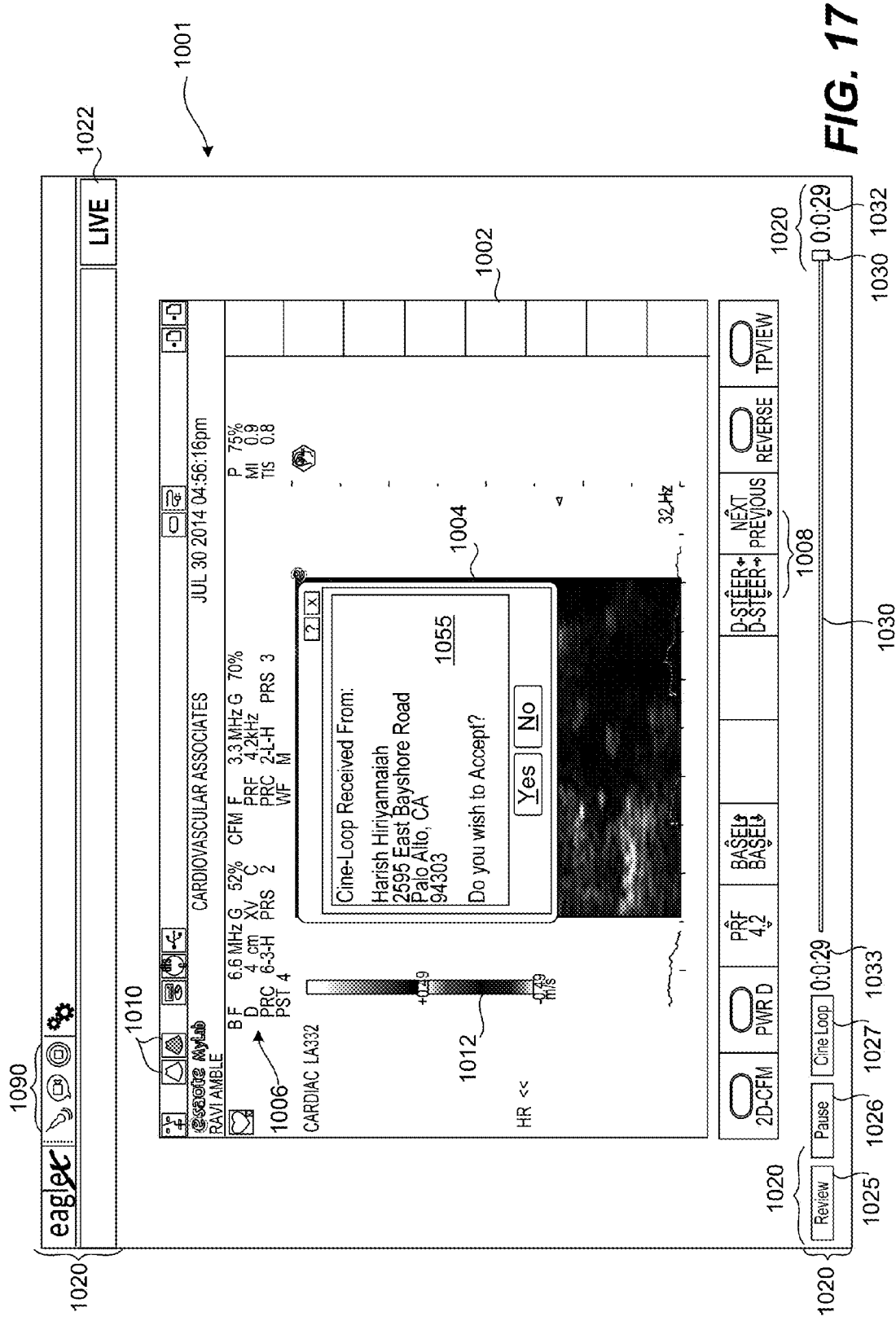

MULTI-SITE DATA SHARING PLATFORM

RELATED APPLICATIONS

The present application is a Continuation-in-Part of earlier filed U.S. patent application Ser. No. 14/292,258, filed May 30, 2014, which is a Continuation-in-Part of earlier filed U.S. patent application Ser. No. 14/214,321, filed Mar. 14, 2014, which claims priority of U.S. Provisional Patent Application No. 61/800,316, filed Mar. 15, 2013. U.S. patent application Ser. No. 14/292,258 also claims priority to U.S. Provisional Patent Application No. 61/829,905 filed May 31, 2013. Each of these priority applications is incorporated by reference in their entirety for all purposes.

FIELD OF THE INVENTION

The present invention relates generally to mechanisms for creating, replaying, annotating and/or sharing selected segments of a biometric imaging or data stream. The described technologies are well suited for use in telemedicine applications during a radiological examination to facilitate real-time collaboration.

BACKGROUND

In the medical field, different medical procedures and examinations require varying levels of expertise. Some examinations and/or procedures can be conducted by a nurse practitioner, while others are typically done by a doctor (in human medicine) or a veterinarian (in the case of animal medicine), while still others require the participation of a highly trained medical specialist. One very specialized medical field is radiology. Radiology is a medical specialty that employs the use of imaging to diagnose and/or treat disease or trauma within the body. Radiologists use an array of imaging technologies including ultrasound, angiography, X-ray radiography, computed tomography (CT), nuclear medicine, positron emission tomography (PET) and magnetic resonance imaging (MRI) to diagnose and/or treat ailments.

In human medicine, the medical practitioner or technician who conducts certain types of medical tests often lacks the expertise to properly interpret the results. As a result, a specialist is contacted to provide a diagnosis based on the results of the examination. For example, the acquisition of medical images is usually carried out by a radiographer or a radiological technician in a radiology lab without a radiologist or the ordering physician being present. Due to the complexity of radiological images, even the surgeons and primary care physicians who order the radiological examination typically cannot independently make a diagnosis based on the radiological images. Rather, a certified radiologist must interpret or "read" the images and produce a report of their analysis, diagnosis, findings and/or impressions. Since the radiologist is most often not present during the radiology session, the images must be sent to the radiologist for analysis after the session has been completed. Once the radiologist has completed their analysis, a report is typically transmitted to the ordering physician—who schedules an appointment at a later date to meet with the patient to discuss the results. If the radiologist sees something that requires further imaging (e.g., to get a different view of a region of interest) a new scan is ordered and the process is repeated. This substantially increases the time and costs involved in conducting the required level of analysis for appropriate diagnosis and healthcare delivery (pre-procedure, post-procedure and timely monitoring).

The process can be sped-up if the radiologist personally conducts the radiological examination or is present during such examination. However, there are a limited number of radiologists and it is often not practical from either a cost or availability standpoint for the radiologist to be physically present during the radiological examination. Therefore, the most common process is to acquire the radiological images in a first session and then transmit the images to the radiologist for review after the radiology session is complete. This problem is amplified in the veterinarian medicine field where there are only a few hundred radiologists that collectively service the needs of tens of thousands of veterinary clinics.

More generally, the need to obtain the assistance of a specialist can introduce substantial delay in the diagnosis of a variety of different types of medical conditions. In some fields of medicine and in some parts of the country, there are a very limited number of specialists available. As a result, in can take weeks to get appointments with the appropriate specialist(s) and arrange for the required lab work (e.g., ultrasound, MRI, CT, PET, EKG, etc.). It is not uncommon for a specialist reviewing test results to request another test or scan. This may be because the test was improperly performed. Alternatively, the results may indicate to the specialist that the test should be performed in a somewhat different manner or that further tests may be appropriate. As a result, both the diagnostic exam/test and the consultation with the specialist must be rescheduled.

Telemedicine has the potential to substantially improve patient care by facilitating more immediate access to highly trained specialists at a variety of stages in the health care delivery process. Accordingly systems that can improve the efficacy of remote medicine are of great interest.

The Applicant has developed a collaborative telemedicine platform that allows a remote medical specialist (such as a radiologist) to participate in an examination in real time. Several unique aspects of that platform are described herein. Although radiological applications are often used as a representative use of the technology, it should be apparent from the following description that the described collaborative telemedicine platform can also be used in a wide variety of other remote patient care and clinical patient care applications.

SUMMARY

A variety of methods and arrangements for sharing medical data are described. In one aspect, multiple data streams are received from one or more medical imaging/sensing devices or other types of devices (e.g., a video camera). Frames are obtained from the data streams. In some embodiments, a part of each frame and/or only particular frames are selectively encrypted. The frames are transmitted to a remote device. The frames for the streams are reconstructed, rendered and/or displayed at the remote device. In various embodiments, the frames of different streams are synchronized.

The streams may involve a variety of different types of media and data, depending on the needs of a particular application. In some embodiments, for example, the streams are a video stream and a biometric imaging stream. One example approach involves performing a biometric imaging scan (e.g., an ultrasound scan) on a patient, which generates a biometric image stream. Concurrently, a video camera is directed at a technician that is using the biometric imaging device, which indicates how the device is being handled and positioned. The video camera generates a video stream. Frames are obtained from the video and biometric imaging streams. The frames are transmitted to a remote device e.g., as a packet sequence. At the remote device, the frames are reconstructed and synchronized. In various embodiments, a user of the remote device can then display and observe the video and biometric imaging in (near) real time. The synchronization helps ensure that the video and biometric imaging are properly timed and coordinated when viewed at the remote device.

Any suitable data streams may be synchronized. In some embodiments, for example, frames are obtained from biometric waveform data and biometric imaging streams received from one or more medical imaging/scanning devices. The frames are transmitted and synchronized. In still other embodiments, annotation data is received from a specialist or medical professional and biometric imaging data is received from a medical imaging/sensing device. Frames are obtained from the annotation data and the biometric imaging data, which is then transmitted and synchronized.

In another aspect, a data stream is received from a medical imaging/sensing device or another type of device. The data stream may be any suitable type of data stream, including a biometric imaging, biometric data, video, audio, annotation data or other type of data stream. Frames are obtained from the stream. At least some of the frames are (partially) encrypted. In some embodiments, only a part of each frame is encrypted. Some implementations involve encrypting only a header of the frame, at least part of a header of a frame or only part of the header and part of the media data (payload) of the frame. The frames are then transmitted to a remote device.

BRIEF DESCRIPTION OF THE DRAWINGS

The invention and the advantages thereof, may best be understood by reference to the following description taken in conjunction with the accompanying drawings in which:

FIG. 13 is a representative screen shot of the window of FIG. 12 after selection of the review mode.

FIG. 14 is a representative screen shot of the window of FIG. 12 in the Cine Loop mode.

FIG. 17 is a representative screen shot of a window showing a dialog box that may be used to inform a collaborator of the availability of a Cine Loop for their review.

In the drawings, like reference numerals are sometimes used to designate like structural elements. It should also be appreciated that the depictions in the figures are diagrammatic and not to scale.

DETAILED DESCRIPTION

The present invention relates generally to methods and arrangements for supporting collaborative telemedicine. The Applicant has developed a collaborative telemedicine platform that allows a remote medical practitioner (who may be a specialist such as a radiologist, a general practitioner, etc.) to participate in an examination in (near) real time. Several unique aspects of that platform are described herein.

In one aspect, a platform is described that allows a practitioner conducting a medical examination and a remote medical practitioner to concurrently share a plurality of different views in real time. By way of example, one of the shared views may be live streamed biometric information (such as radiological images, biometric waveforms, etc.). Another shared view may show a relevant view of the patient being examined. One example of this might be a view showing the placement and orientation of an ultrasonic probe being used in a sonographic examination. Other shared views may include items such as video conference type view of one of the participants, a replay of an imaging stream selected by one of the participants, reference materials (e.g., use cases for healthcare lifecycle management) that have been selected by one of the participants, etc. Several unique aspects of that platform are described herein. A particular strength of the platform is the ability to share medical imaging streams (such as the output of an ultrasonic probe) with remote collaborators in real time as the examination is taking place. Although radiological applications are often used as a representative use of the technology, it should be apparent from the following description that the described collaborative telemedicine platform can also be used in a wide variety of other remote medicine applications as well.

Figure 1:
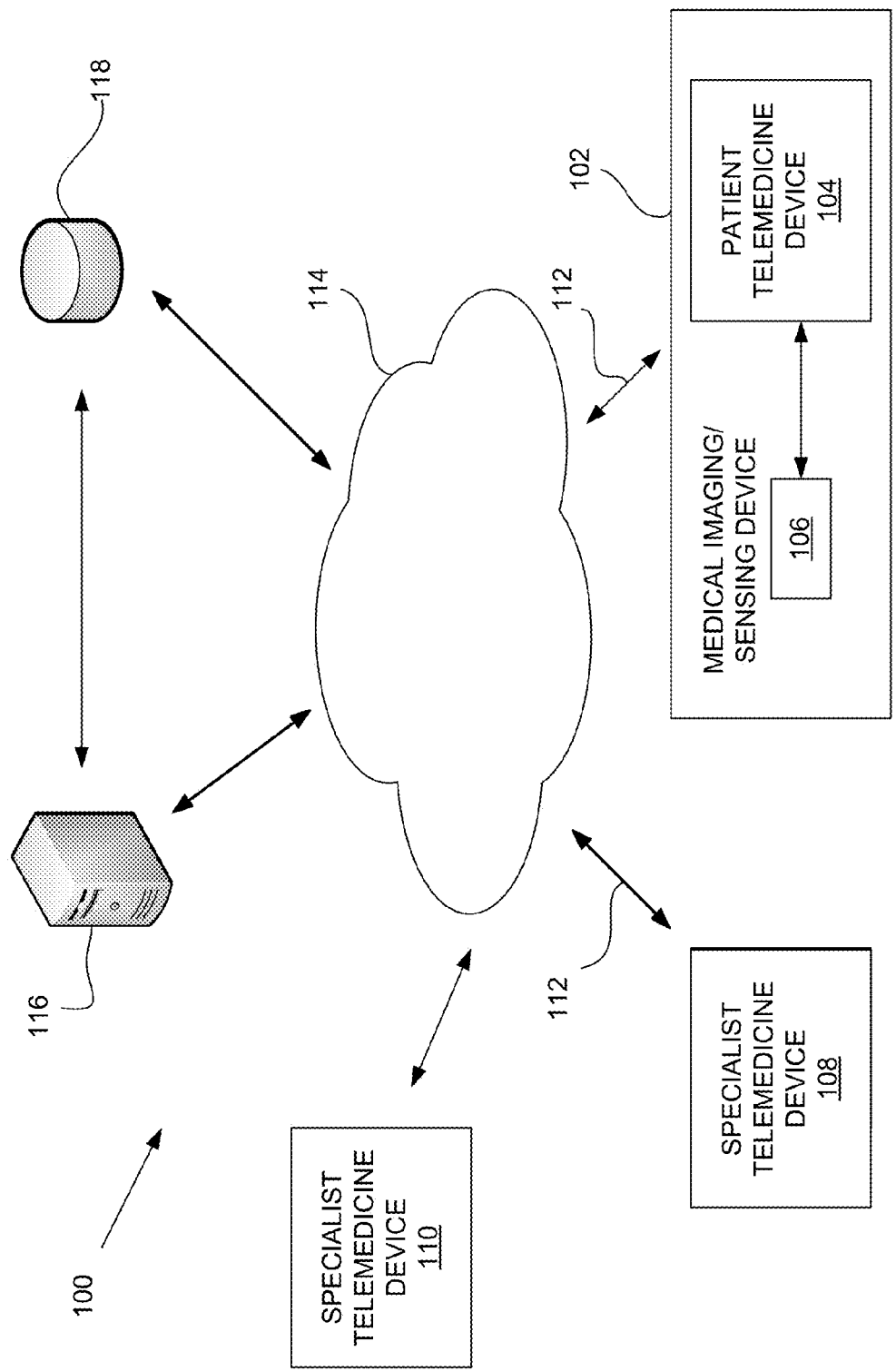
FIG. 1 is a block diagram of a multi-site data sharing platform according to a particular embodiment of the present invention.

Referring initially to FIG. 1, a multi-site data sharing platform 100 according to a particular embodiment of the present invention will be described. The platform 100 includes first and second telemedicine devices (workstations) 104, 108. For convenience, the first telemedicine workstation 104 is sometimes referred to herein as the "patient" or "local" telemedicine workstation since it is preferably positioned at the location of a patient and is used by a technician or practitioner that is interacting with the patient. The second telemedicine workstation 108 is sometimes referred to herein as the "remote" or "specialist" telemedicine workstation since it is typically positioned at a location that is apart from the patient and is most often used by a medical practitioner (such as a specialist, the ordering doctor, etc.) that is participating in the telemedicine session. Optionally, one or more additional remote telemedicine workstations 110 may be included for use by others that are participating in or viewing the telemedicine session. Such remote participants may include other specialists that are participating to provide a second opinion, other medical practitioners involved in the patient's care (e.g., the ordering physician/veterinarian, a surgeon that will be operating on the patient, the patient's primary care physician, etc.), parties that are observing the examination for training or educational reasons (e.g., interns, residents, students trainees, etc.) or anyone else that has a reason to participate in the examination.

The telemedicine workstations 104, 108, 110 are connected to one another through one or more networks 112 and may optionally also be connected to a cloud based architecture 114. The cloud based architecture 114 preferably includes one or more servers 116 and one or more databases 118 which optionally include a medical records store 117, a use case library 119 and various other databases. Any suitable network(s) may be used to connect the devices of the platform, including but not limited to local area networks, wide area networks, intranets, the Internet, etc.

The patient telemedicine workstation 104 may be located at a clinic 102 that includes one or more medical imaging/sensing devices 106 that communicate with the patient telemedicine workstation 104. The telemedicine devices typically take the form of a general purpose computing device having software configured to perform the described functions—although special purpose devices can be used as well. Suitable computing devices include desktop computers, laptop computers, tablet computing devices, mobile devices, etc. Alternatively, the function of a local workstation 104 can sometimes be incorporated into a sensing device such as a radiological imaging device (e.g., an ultrasound machine, a CT scanner, an MRI scanner, etc. Typically, the workstations include one or more displays, one or more processors and memory suitable for storing the software (computer code) that provides the described functionality as well as memory suitable for storing and/or caching data used by such software including received biometric or imaging streams.

The patient telemedicine workstation 104 is arranged to obtain (and optionally store) data from each connected medical imaging/sensing device that is being used for diagnostic testing. In many circumstances, the data received from a particular source will be received in the form of one or more live streams (e.g. a sonographic stream, or a multiplicity of sensor outputs from an EKG machine). Generally, the patient telemedicine workstation 104 is situated near a patient who is currently undergoing the diagnostic testing, although this is not a requirement. The patient telemedicine workstation 104 encodes the data streams from the diagnostic testing and transmits them to other participating telemedicine devices (e.g., remote telemedicine workstation 108). As a result, users of those remote telemedicine devices are able to view and participate in the diagnostic test in (near) real time. That is, the media received at the remote telemedicine devices is generally rendered live, although there may be some small delay due to the inherent latencies caused by network conditions and overhead. The telemedicine workstation also allows a medical professional at the site of the diagnostic test to communicate with professionals who are participating in the telemedicine session remotely.

The patient telemedicine device 104 is preferably arranged so that it may be coupled to (or otherwise receive inputs from) a variety of different types of biometric diagnostics machines. These may include various types of imaging devices (e.g., ultrasound probes, X-ray machines, MRI devices, CT scanner, etc.) and/or biometric measurement devices (e.g., EKG, EEG, or ECG devices; pulse oximeters; thermal/temperature sensors; blood pressure monitors; glucose level monitors; pulmonary function testers, etc.). Although the workstation 104 can preferably be coupled to a variety of different types of diagnostic machines, it is most often connected to a single imaging machine during any particular radiological examination. In some circumstances it may be desirable for the workstation to be simultaneously coupled to more than one biometric device, as for example, an imaging device and a biometric measurement device, or multiple biometric measurement devices.

The patient telemedicine device 104 is also arranged to provide an audio and one or more video links with the remote telemedicine devices. The audio link allows the practitioner(s) who are working with the patient to talk with the remote participants. The video links originating from the patient side allow remote participants to view relevant aspects of the examination. In various embodiments, a video camera is attached to the device 104 to provide video of the procedure that may be shared with the remote participants. The appropriate focal point of the camera will vary with the needs of any particular examination. Most often, a camera will be focused on the examination target. For example, during an ultra-sound examination, a camera may be focused on the area that the ultrasound probe is being applied to so that remote participants can see how the operator is positioning and otherwise using the probe simultaneously with viewing the images produced by the probe. In other situations the telemedicine workstation 104 may be arranged to receive a video feed from a camera associated with a scope (e.g. an endoscope, an otoscope, etc) during an procedure. Sharing such streams allows the remote participants to see the video output of the scope.

There are times when the operator of the patient telemedicine workstation 104 will want to view various types of supplementary information that may be helpful in the diagnostic/medical procedure. To facilitate this, the system has access to use cases, medical records, reference imagery and other types of data that may be helpful in the diagnostic/medical procedure. In various embodiments, such data is downloaded through the cloud based architecture 114 from the server 116 and/or the database 118 or use case library 119 to the patient telemedicine system 102.

Depending on the preferences of the operator of the patient telemedicine system 102, some or all of the above data is selectively presented in a display that is connected to or part of the system 102. Preferably, the patient telemedicine device 104 has a graphical user interface that allows the operator to select and simultaneously display a plurality of different items as different views. The different views may be rendered in different windows, in different panes of a window, or in any other suitable manner. As will be described in more detail below, the operator may select the views that are deemed appropriate at any time. By way of example, when used in conjunction with an ultrasound imaging machine, one window may display the ultrasound image live. A second window may show the output of video camera 106a and a third window may display a video conference feed from a remote participant. A fourth window may be arranged to show a patient's medical record or other information of use to the operator. An advantage of locally displaying the locally generated biometric and video feeds is that it allows the operator to see what is being shared with remote participants. In another example, the operator can arrange to have biometric images (e.g., an ultrasound scan displayed in real time) presented in one window of a display screen and biometric data (e.g., waveform results from an EEG) in another window. A video of a remote collaborator might be presented in a third window, and a fourth window can include a medical record and/or reference imagery (e.g., if the ultrasound scan shows a diseased heart, the fourth window may include a reference image of a healthy heart or a similarly diseased heart).

In various embodiments, an operator of the patient telemedicine workstation 104 is able to annotate any of the displayed images, waveforms or test results. In some implementations, for example, the operator can provide input (e.g., circle or otherwise mark a portion of an image displayed on a touch-sensitive screen) indicating that a particular image part should be highlighted or examined further. This annotation data is also selectively transmitted to other remote collaborators in the platform.

The operator can selectively designate which of the above types of data should be transmitted or shared with other remote collaborators in the multi-site data sharing platform 100. The patient telemedicine device 104 obtains or generates frames from the shared data, selectively encrypts, multiplexes and/or transmits them through the network to the other collaborator(s) and telemedicine workstation(s).

Each remote telemedicine device 108/110 receives the frames and is arranged to render them in real time. The various media streams may be shown on one or more display screens at the remote telemedicine device. The operator of each remote telemedicine device 108/110 can configure how the various types of media are displayed. For example, if the patient telemedicine device transmits biometric imaging data, waveform data, video data, an audio stream and patient records to the remote telemedicine device 108/110, the operator of the remote telemedicine device can display the waveform data in one window on the display screen, the biometric imaging data in another window, the video data in a third window, and the patient records in a fourth window. Received audio communications will be played through a speaker associated with the remote telemedicine device 108. Generally, the various media streams are received simultaneously, in real time, and rendered at nearly the same time and order as they are received or displayed at the patient telemedicine device 104.

The operator of the remote telemedicine device 108/110 can also provide input to the device, which is transmitted in real time to other collaborators in the platform 100. By way of example, the operator can annotate any received biometric image, waveform or test result or select a relevant segment of a stream for review (e.g., create a short video segment or "cine-loop") and any of these items can be shared with other collaborators. (Stream segments that are typically rendered in the form of a short video sequence that is repeatedly replayed are sometimes referred to herein as "cine-loops"). The operator can also speak with other participants over an audio channel. The operator can also obtain use cases, medical records, reference imagery and any other suitable diagnostic aids or information from the cloud-based server 116 and/or the database 118 or use case library 119. When appropriate, the operator can elect to share any of these inputs with other participants in the telemedicine session. Shared media (i.e., annotation data, medical records, use cases, audio messages, etc.) are then transmitted to the patient telemedicine device 104 and/or any other designated devices in the platform, so that they can be rendered and displayed in real time at those devices.

The above system allows a specialist to use a remote workstation 108/110 to fully participate in the aforementioned diagnostic procedure. In various embodiments, for example, the specialist telemedicine workstation 108/110 receives ultrasound imagery. Simultaneously, the specialist also receives a video indicating how an ultrasound probe is being handled to produce the ultrasound imagery. The specialist is thus able to review the procedure in real time. Thus, the specialist has the ability to provide feedback to the medical professional who is handling the ultrasound probe or equipment. For example, the specialist can request that the attending medical professional reposition an ultrasound probe on a particular portion of the patient's body to get a better or different view of a region of interest.

The server 116 is arranged to facilitate communication between participants in a telemedicine session. In some embodiments, particularly in implementations in which there are only two participants (e.g., the patient telemedicine device 104 and a single specialist telemedicine device 108), the server 116 is not necessary. In other applications, however, there may be more than two participants. For example, there may be a second specialist who is using another specialist telemedicine device 110 to also participate in and observe the diagnostic procedure. In some embodiments, some or all traffic between multiple telemedicine workstations passes through the server. The server 116 helps ensure that each participating device has access to any data that is shared by any other device.

The server 116 can provide a variety of additional features, depending on the needs of a particular application. Various implementations involve the server 116 providing a store and forward and broadcasting functionality. That is, any data that is to be shared and is transmitted from a device is first transmitted to the server, which stores the data and then forwards copies of the data to the intended recipients. In some embodiments, the server 116 and/or its connected database(s) 118 store copies of some or all traffic transmitted between the devices in the platform. Upon request from any properly authorized device (e.g., patient telemedicine device 104 and specialist telemedicine device 108/110), the server 116 and/or the database 118 can provide previously transmitted imagery, test results, annotations or any other transmitted data which can be a powerful diagnostics tool.

Figure 2:
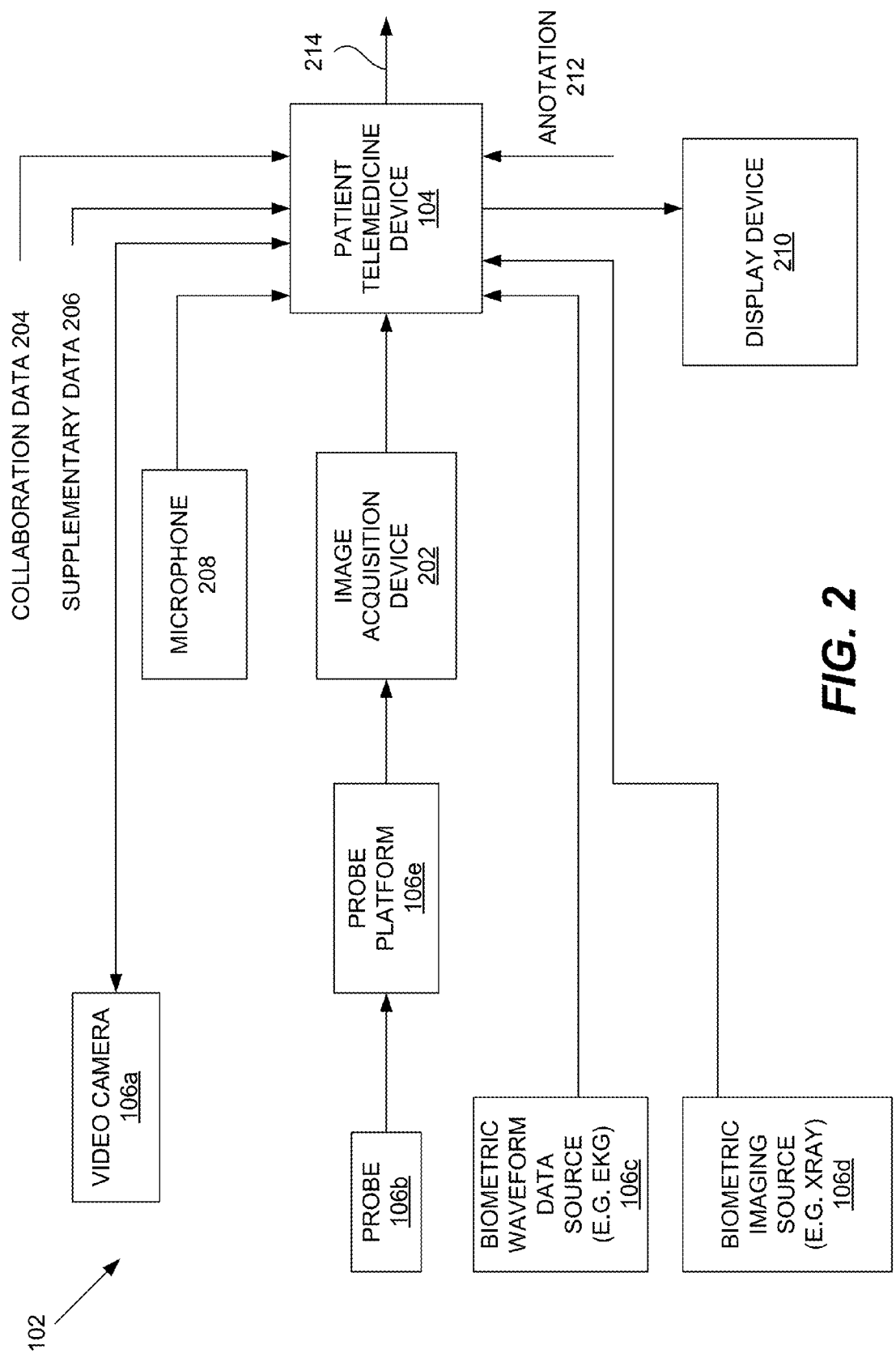
FIG. 2 is a block diagram of a patient telemedicine system according to a particular embodiment of the present invention.

Referring next to FIG. 2, a representative embodiment of the patient telemedicine workstation 104 of FIG. 1 will be described. The patient telemedicine workstation 104 is arranged to collect data streams from various medical imaging/biometric sensing devices 106a-106e that are being used on a patient, process the streams, and transmit them to designated recipients, such as a specialist. In the illustrated embodiment, the patient telemedicine workstation 104 has the ability to receive inputs from a variety of different devices such as a video camera 106a, a probe 106b, a probe platform 106e, an image acquisition device 202, an electrocardiogram (EKG) device 106c, an X-ray device 106d and a display device 210. It should be noted that the figure is intended to be illustrative and exemplary and that any number or combination of components, medical imaging/sending devices and tools may be used. All of these devices are connected with and transmit data to the patient telemedicine device 104.

The video camera 106a represents one or more video cameras used to take video footage of an area of interest, a medical scanning/sensing device, a patient, a technician and/or an operator of the telemedicine device 104. In various embodiments, for example, the video camera 106a is directed at a medical scanning/sensing device (e.g., an ultrasound probe) and/or a particular region (e.g., the hand of a technician that is gripping the probe and/or a portion of the patient's body where the probe is being applied, such as the chest or abdominal area.) Thus, the video footage can be used to observe how the medical scanning/sensing device or probe is being applied to a patient, and a viewer of the footage can make recommendations on how the device should be used or repositioned. Alternatively or additionally, a video camera 106a is directed at an operator, medical professional or other person who is participating in the telemedicine session from the side of the patient. A video camera 106a may also be taking video footage of the patient. The video data is streamed to the patient telemedicine device 104 in (near) real time.

The probe 106b represents any type of medical imaging/sensing device that is operated and handled by a medical professional. An example of such a probe is an ultrasound probe, which is a wand or other device that emanates ultrasound waves and is typically placed against the body of a patient to provide a scan of a particular portion of the patient's body. The probe 106b is attached to a probe platform 106e, which is arranged to collect the image data. An image acquisition device 202 is attached to the probe platform 106e and is arranged to obtain the biometric image stream generated by the probe platform 106e. The image acquisition device 202 is in turn connected to the patient telemedicine device 104 and transfers the biometric image stream to the telemedicine device 104, so that it can be encoded and transmitted, as desired, to a remote telemedicine device (e.g., specialist telemedicine device 108/110) and other participants in the telemedicine session.

The electrocardiogram device 106c is arranged to monitor the electrical activity of the heart of the patient. In various embodiments, an electrocardiogram involves attaching multiple electrodes to the body of the patient. The electrodes monitor the electrical activity in the body and an electrocardiogram device generates waveforms to indicate this electrical activity. The electrocardiogram device transmits this waveform data to the telemedicine device 104. The electrocardiogram device 106c may represent any number of suitable devices that are arranged to collect biometric data that tracks or reflects physiological changes in the patient. Such devices include but are not limited to an electroencephalography (EEG) device, a temperature detection device, a blood pressure device, a glucose level detector, a weighing device, a pulmonary function test device and a pulse oximeter.

The X-ray device 106d is arranged to project X-rays towards a patient and obtain X-ray images of portions of the patient's body. Any device suitable for obtaining biometric image data may be added to or replace the X-ray device. Such devices include but are not limited to a CT scanner, an MRI device, a retinal scanner, an ultrasound scanning device or any nuclear medicine-related device. The X-ray device generates biometric imaging data, which is also transmitted to the telemedicine device 104.

The patient telemedicine device 104 coordinates the operation of the other components of the patient telemedicine system 102. The patient telemedicine device 104 collects data from multiple sources and medical imaging/biometric sensing devices, displays the data, makes requests for additional data, receives input from an operator and shares selected types of data with other participants in a telemedicine session. Any suitable type of computing device may be used. In some embodiments, for example, the patient telemedicine device 104 is a laptop, computer tablet, a mobile device and/or a desktop computer.

In addition to the imaging, waveform and other types of medical data described above, the patient telemedicine device 104 can also receive a variety of other types of data from the cloud based architecture 114 and/or from an operator of the device 104. In various embodiments, there is an audio channel or messaging system that allows an operator to communicate with other participants in the telemedicine session by speaking into a microphone 208 that is connected to the patient telemedicine device 104. Additionally, the operator can provide input to the telemedicine device 104 to request supplementary data 206. The telemedicine data then transmits a request for such data to the cloud-based server 116 and/or database 118. The supplementary data is any suitable diagnostic or reference data that will assist in the diagnostic procedure. The supplementary data 206 includes but is not limited to use cases, reference imagery (e.g., ultrasound images of healthy or unhealthy tissues in the body, etc.), medical records for the patient, descriptions of various medical diseases and conditions, etc. Upon request, the server 116 transmits the requested supplementary data to the patient telemedicine device 104.

The patient telemedicine device 104 may also receive collaboration data 204 from other devices in the same telemedicine session (e.g., specialist telemedicine device 108/110 of FIG. 1.) The collaboration data 204 includes any suitable data that a remote specialist or operator chooses to share with the rest of the participants in the telemedicine session, including but not limited to annotations, audio messages, selected use cases, reference imagery and medical records.

The patient telemedicine system 102 includes a display device 210, which is part of or connected to the patient telemedicine device 104 and may be any suitable video screen or user interface suitable for presenting test results and media. The operator of the telemedicine device 104 can select which, if any, of the above types of data should be displayed at the display device 210.

Figure 4:
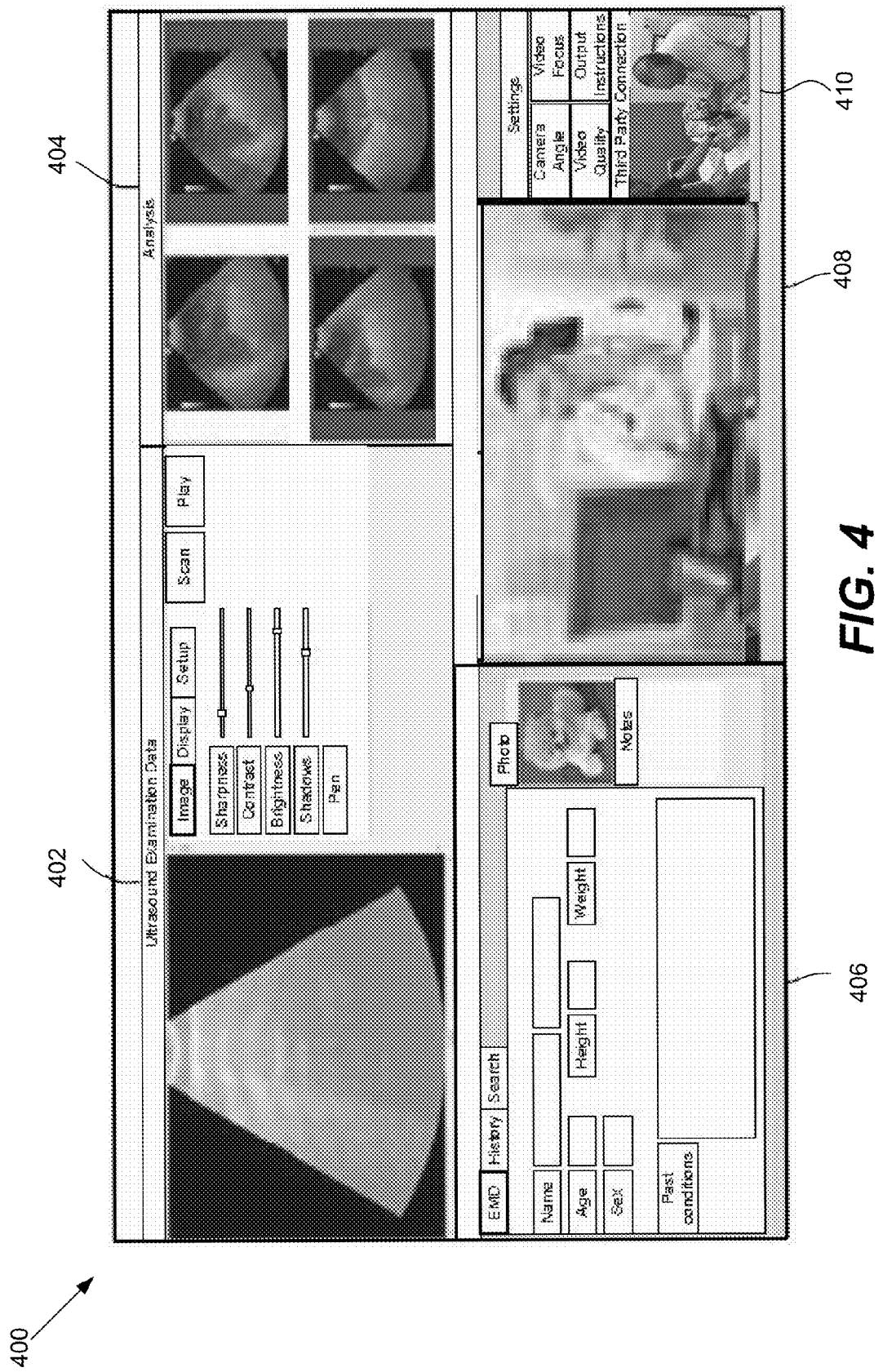
FIG. 4 is an example user interface for the patient telemedicine device illustrated in FIG. 2.

One example user interface 400 displayed in the display device 210 is illustrated in FIG. 4. The user interface 400 includes multiple windows, including windows 402, 404, 406, 408 and 410. In various embodiments, the operator of the telemedicine system 104 is able to configure the user interface 400 in accordance with his or her preferences. For example, some of the received imaging, waveform, supplementary or collaboration data may be excluded from the user interface, while other selected media is shown. Each type of media can be shown in a separate window, which can be resized and moved as desired by the operator.

In the illustrated embodiment, for example, an image from an ultrasonic scan, taken using the probe 106b, is displayed in the window 402. In this case, the image is a snapshot from an ongoing ultrasound scan of a dog. The image is constantly received and updated in (near) real time as the scan continues. The medical records for the pet, which was downloaded as supplementary data from the cloud-based server, is presented in window 406. A (near) real time video of a technician performing the ultrasonic scan is shown in window 410. This video was obtained from a video stream generated by the video camera 106a. Also, in window 408, a real time video of a specialist using the specialist telemedicine device 108 is shown. This video is collaboration data that was transmitted by the specialist telemedicine device 108 for display at the patient telemedicine system 102.

In another window 404, various reference ultrasound images are presented that are used to provide a comparative model for the ultrasound imagery in window 402. In some embodiments, the patient telemedicine device 104 requests and receives such images from the cloud-based server 116 or database 114. In other embodiments, the patient telemedicine device 104 receives a message from a specialist (i.e., through a specialist telemedicine device 108/110), which identifies imagery or other data that is stored in the cloud and should be reviewed. In response to the message, the user can provide input to the patient telemedicine device 104, which triggers the downloading of the images from the cloud-based database 118 for display at the display device 210.

In this example, the media in windows 402, 408 and 410 are received in real time from various connected medical imagery/biometric sensing devices (e.g., the probe, the video camera) or from a specialist telemedicine device 108/110. Additionally, any suitable type of collaboration data received from a specialist is generally also received and displayed in real time. For example, the video of the specialist in window 408 can display, in real time, the face of the specialist, since face-to-face conversations are sometimes desirable and can facilitate communications between the participants in the telemedicine session. This video is constantly and progressively transmitted by the specialist telemedicine device 108 to the patient telemedicine device 104 over the network.

Some implementations allow an operator to annotate any of the images displayed in the user interface. In various embodiments, the operator is able to mark, circle or highlight any of the windows. The operator can provide such marks by, for example, touching or swiping a touch sensitive screen, applying a pen to the screen, or by providing keyboard or other types of input. The patient telemedicine device 104 receives the annotation data 212 and associates it with the frames, data or images upon which the marks were made. This information can then be transmitted in real time to other devices in the multi-site data sharing platform (e.g., the specialist telemedicine device), so that they may review the markings as they are made.

The operator of the patient telemedicine device 104 can then provide input to the device 104, indicating which types of the aforementioned data (e.g., biometric imaging data, annotation, video, audio, etc.) should be shared with one or more other devices in the platform. Alternatively, this sharing selection process may be automated, possibly based on settings that were configured by the operator beforehand. The patient telemedicine device 104 then encrypts selected frames of the selected streams. In various embodiments, the frames are broken down into packet sequences 214, which are multiplexed and/or transmitted to a device 108/110 and/or to the server 116 for distribution throughout the multi-site data sharing platform 100. The frames are then reconstructed at those remote devices for rendering at the devices.

Figure 3:
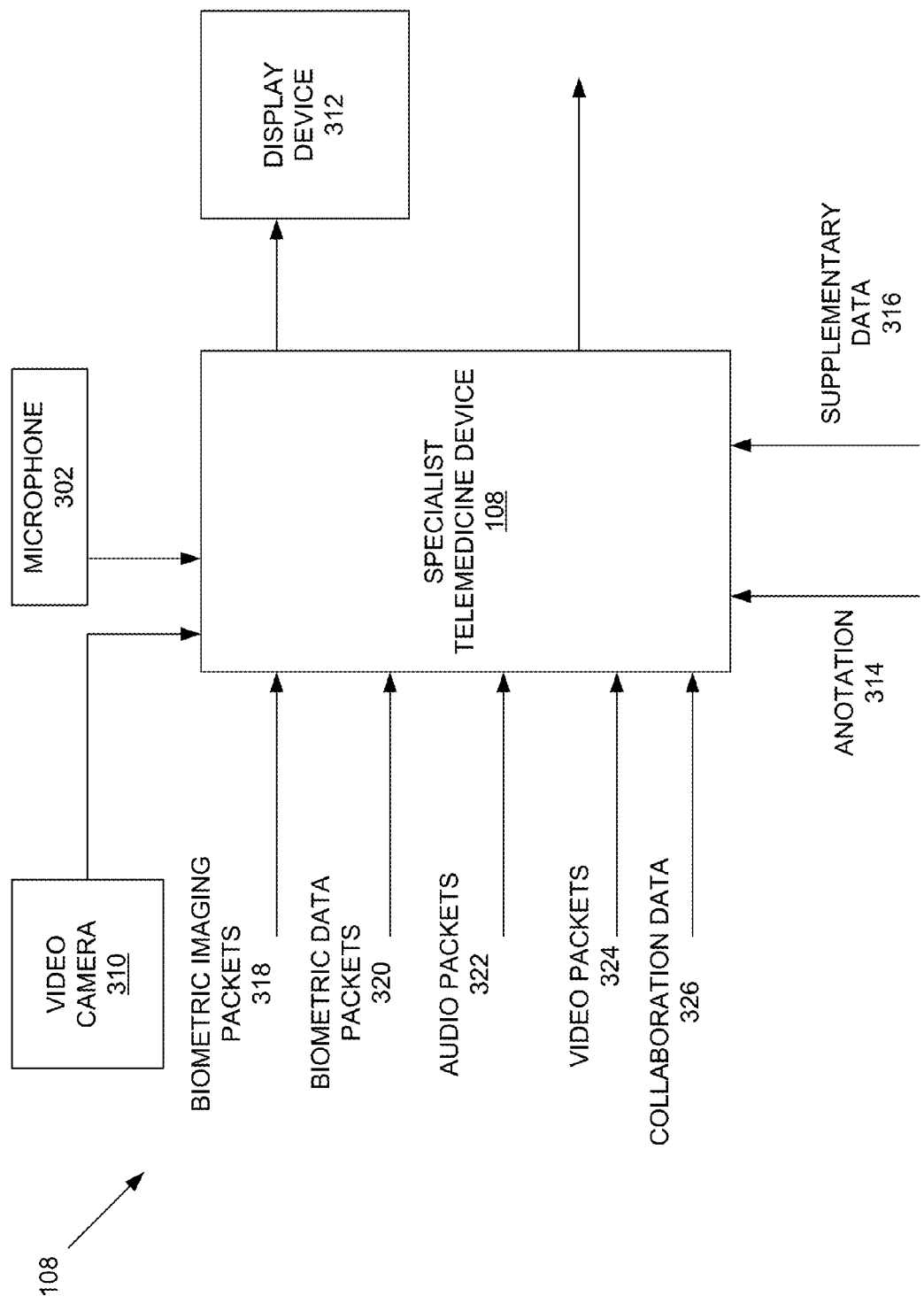
FIG. 3 is a block diagram of a specialist telemedicine device according to a particular embodiment of the present invention.

Referring next to FIG. 3, the specialist telemedicine device 108 illustrated in FIG. 1 will be described. The specialist telemedicine device has an associated memory or storage unit 109 and includes or is connected to a video camera 110, a microphone 302 and a display device 312. In the illustrated embodiment, the specialist telemedicine device 108 is used by a specialist (e.g., a radiologist) whose expertise is desired by a user of the patient telemedicine device 104. In some situations, another medical practitioner (e.g., a family doctor for the patient) uses the remote telemedicine 108 to remotely observe the diagnostic procedure. The remote telemedicine device 108 may be any suitable computing device, including but not limited to a computer, a laptop, a computer tablet and a mobile device.

The remote telemedicine device 108 receives the packet sequences 214 and reconstructs the frames of the data (e.g, biometric imaging data, annotation, video, audio, etc.) The frames can then be rendered and the various types of data can be displayed. The operator of the specialist telemedicine device 108 can provide input to the device, indicating which types of media and data should be displayed at the display device 312. The display device 312 may use any suitable user interface, screen or display technology, including but not limited to a video screen, a touch sensitive screen and an e-ink display. In various implementations, different types of data are shown in separate windows or sections on a user interface 500 displayed on the display device 312.

The specialist telemedicine device 108 receives and/or stores the various packet sequences. The operator of the specialist telemedicine device 108 can provide input to the device, indicating which types of media and data should be displayed at the display device 312. The display device 312 may use any suitable user interface, screen or display technology, including but not limited to a video screen, a touch sensitive screen and an e-ink display. In various implementations, different types of data are shown in separate windows or sections on a user interface 500 displayed on the display device 312.

Figure 5:
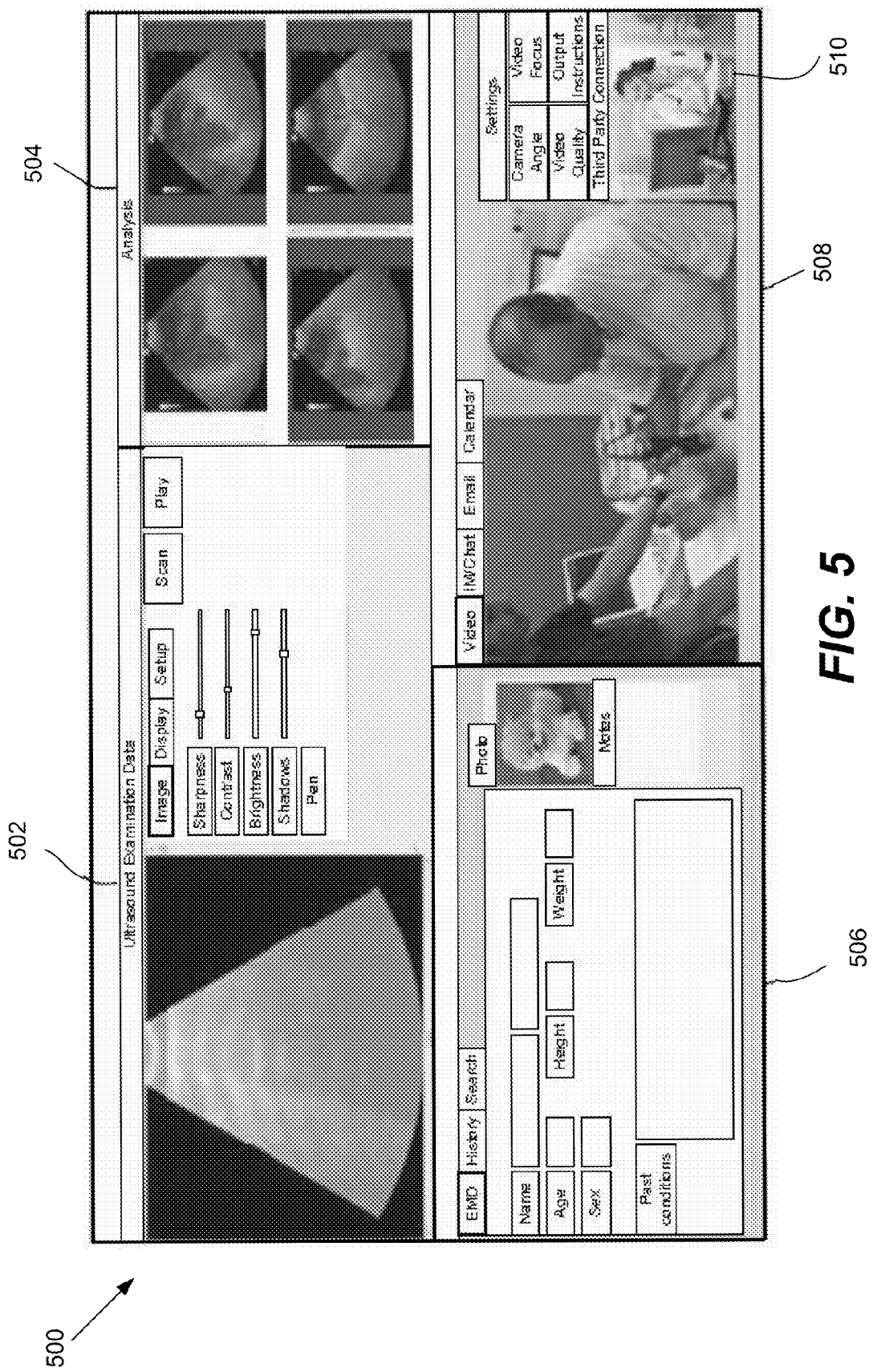
FIG. 5 is an example user interface for the specialist telemedicine device illustrated in FIG. 3.

An example user interface 500 is illustrated in FIG. 5. The user interface 500 includes multiple windows 502, 504, 506, 508 and 510. Different types of media are shown in separate windows. By way of example, an ultrasound image is shown in windows 502. A video of an ultrasonic probe being applied to the body of a patient is shown in window 508. A video of the specialist at the specialist telemedicine system 108 is shown in window 510. The operator of the specialist telemedicine device 108 may configure, resize, move and select media for each window as described in connection with the user interface FIG. 4. In some embodiments, the operator can remotely control the camera generating the video in window 508, allowing the operator to zoom in or out or focus the video camera at different areas of interest, which then adjusts the video in window 508 accordingly and in (near) real time.

It is assumed that the user interface 500 of FIG. 5 is being presented at approximately the same time that the user interface 400 of FIG. 4 is being presented at the patient telemedicine system. As previously discussed, in the example illustrated in FIG. 4, the display device 210 for the patient telemedicine system 102 is displaying an ultrasound image and a video of an ultrasound scanning procedure in (near) real time as the image is being generated at the probe 106*b* and as the ultrasonic scan is being performed. These biometric imaging and video streams have been transmitted to the specialist telemedicine device 108, so that they may be displayed (nearly) simultaneously in windows 502 and 508 of the user interface 500. Thus, an operator of the specialist telemedicine device is able to observe the biometric images and the handling of the biometric imaging equipment at the patient telemedicine system 102 in (near) real time.

Windows 504 and 506 display the supplementary data 316 (reference images and medical records) described in connection with the user interface 400 of FIG. 4. In some situations, the specialist using the specialist telemedicine device 108 initially requests the supplementary data. In that case, the specialist provides input to the specialist telemedicine device 108, which causes the device 108 to send a request for the selected data to the cloud-based server 116 and/or database 118. The desired supplementary data is then downloaded into the device 108 and presented in a user selected window of the user interface 500. Alternatively, another professional at a remote device (e.g., patent telemedicine device 104) may have been the first to suggest the use of the supplementary data. In that case, the remote device (e.g., the patient telemedicine device 104) transmits a message to the specialist telemedicine device 108 recommending particular types of supplementary data which are available in the cloud-based architecture 114. In response, the operator of the specialist telemedicine device 108 provides input to the device 108, which causes the device 108 to retrieve the suggested data and display it at the display device 312.

It should be appreciated that all of the packet sequences for the various types of data (e.g., biometric imaging data, biometric data, waveform data, video, audio, etc.) are received simultaneously and optionally rendered and displayed in (near) real time at the display device 312. This allows the specialist to review the images as they are being generated (e.g., at the patient telemedicine system) and/or follow the diagnostic procedure as it is taking place. Additionally, audio messages from any other device in the platform 100 are played over a speaker, allowing the specialist to listen to commentary from other participants in the telemedicine session.

The specialist telemedicine device 108 allows the specialist to create and share audio messages, make annotations, obtain and suggest supplementary data. Generally, such operations are handled in a similar or the same manner as with the patient telemedicine device 104 of FIG. 2. That is, the operator of the specialist telemedicine device 108 can mark or annotate any displayed images or information, recommend use cases, reference images or other types of supplementary data, and create audio messages using the microphone 302. Additionally, the telemedicine device 108 can include a video camera 310, which can take video footage of the specialist or any other suitable target. The operator of the specialist telemedicine device 108 can provide input to the device, identifying which of the above data that should be shared. The operator can further provide input to the device 108 indicating which devices (e.g., another specialist telemedicine device 110, the patient telemedicine device 104, etc.) in the telemedicine session should receive the selected data. (In various embodiments, the operator makes such selections prior to the beginning of the telemedicine session. During the session, different types of data are then automatically shared and transmitted based on the selections.) The selected data (e.g., annotations, recommended supplementary data, etc.) is progressively transmitted as it is created to the designated recipient devices, so that it can be selectively displayed in (near) real time at those devices.

Figure 6:
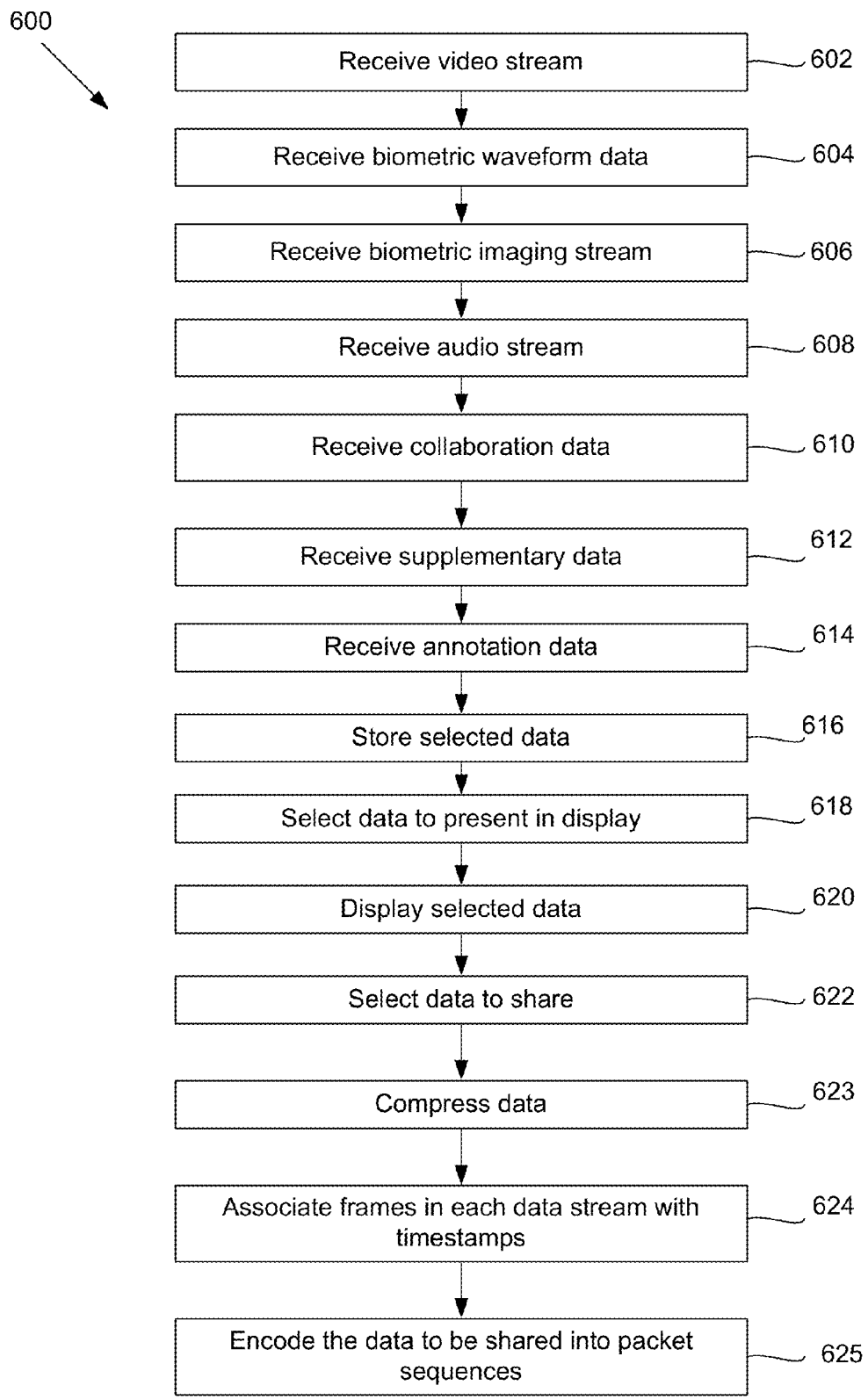
FIGS. 6 and 7 are flow diagrams illustrating a method for receiving, encoding, encrypting and transmitting data streams according to a particular embodiment of the present invention.
Figure 7:
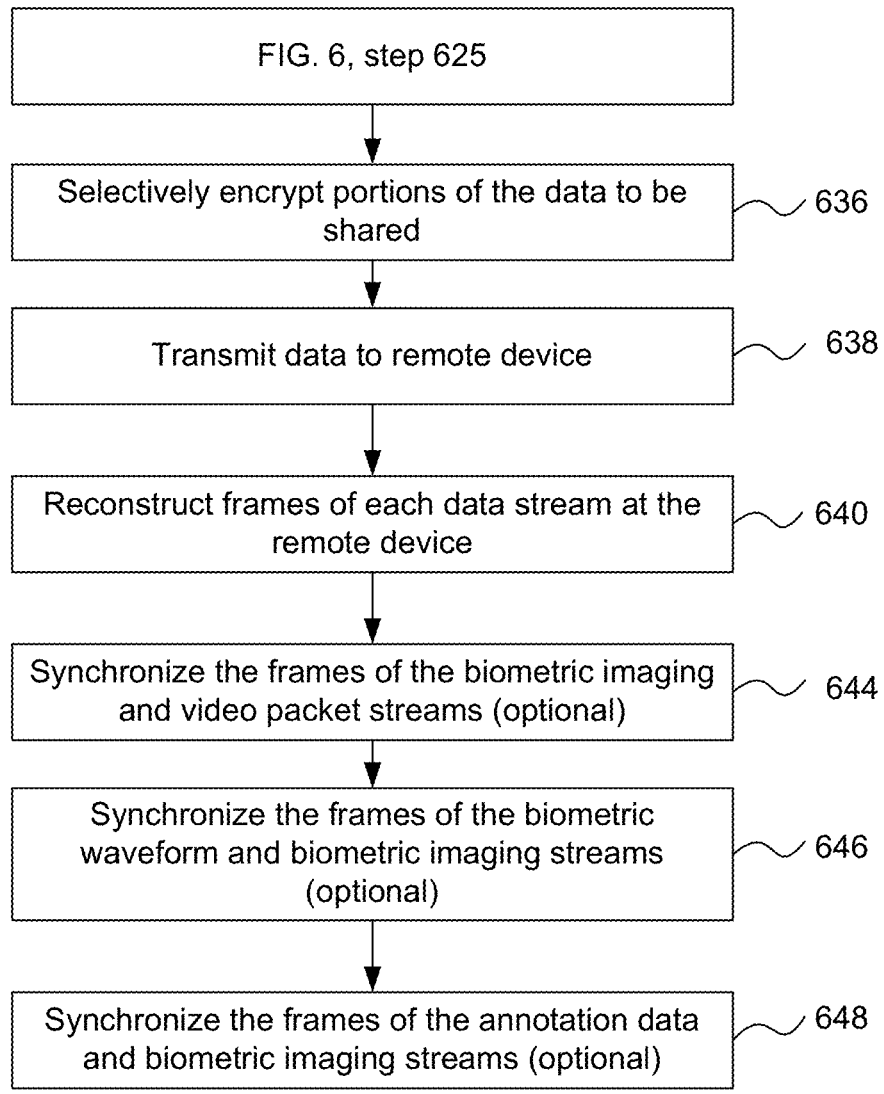

Referring next to FIGS. 6-7, a method 600 for receiving, encoding and transmitting data streams according to a particular embodiment of the present invention will be described. Generally, the method 600 is performed where diagnostic testing is taking place i.e., at the patient telemedicine system 102 of FIG. 2. When multiple data streams are received from various medical imaging/sensing devices, they can be separately encoded, compressed and/or encrypted based on their individual characteristics. Selected streams can also be synchronized, so that telemedicine participants at remote devices can view multiple images, waveforms and video in the appropriate order and in (near) real time.

At steps 602, 604, 606 and 608, the patient telemedicine device receives one or more data streams simultaneously from various imaging/sensing/video devices. For example, a video camera 106a takes video footage of an area of interest (e.g., a part of the body where an ultrasound probe is being applied) and streams the footage to the device (step 602). A suitable medical sensing device (e.g., an EKG 106c, a heart monitor, a blood pressure monitor, etc.) monitors a medical condition of a patient and transmits biometric waveform data to the device 104 (step 604). In various embodiments, a medical imaging device (e.g., an ultrasound scanner and probe 106b) collects images from the patient and sends them to the device 104 (step 606).

Any combination of data streams may be received at the device. By way of example, one useful combination involves an ultrasound probe and a live video camera feed. The video camera that provides the feed is directed at an ultrasound probe and/or a part of a patient's body where the ultrasound probe is being applied. That is, the video camera is oriented so that it can capture where and how the probe is being positioned on the body of the patient. In addition to this live video feed, ultrasound imagery that is generated by the ultrasound probe and its associated equipment is also transmitted in (near) real time to the device 104. When the video feed and the ultrasound imagery is transmitted to a remote device (e.g., specialist telemedicine device 108/110), a specialist at the remote device can observe the medical procedure and make useful suggestions (e.g., request a repositioning of the probe or a different use of the probe) that can immediately be acted upon by the medical professional who is handling the probe.

It should be noted that the above data streams are generally transmitted in (near) real time. That is, data streams are progressively transmitted while the streams are generated and one or more diagnostic tests are ongoing. When a medical imagery/sensing device detects a change in a physiological condition of the patient, this event is immediately registered with the patient telemedicine device in the form of a change in a transmitted medical image, waveform or data. These images, waveforms or data are also selectively displayed in real time on a display device 210 (step 620).

Put another way, it is common that multiple, different types of data that are displayed on the display device 210 will simultaneously indicate a change that is caused by the same physiological change(s) in the patient. By way of example, consider a situation in which an ultrasound scan of a patient's heart is being performed. At the same time, a heart rate monitor is being used on patient. A video camera takes footage of the patient while they are undergoing a medical examination. If the patient begins to hyperventilate, this physiological change will impact all of the above sensing devices. That is, a waveform generated by the heart rate monitor will indicate a rise in beats per minute. The video camera footage indicates a tremor in the patient. The ultrasound scan reveals a quickening in the activity of the heart. Data indicating these changes are received simultaneously at the patient telemedicine device 104 and the aforementioned changes are immediately and simultaneously represented at the display device 210 in the form of changes in the heart rate waveform, the video footage and the ultrasound imagery. As will be discussed later in this method 600, two or more of these data streams will be encoded and synchronized, so that this timing is also conveyed to any remote participants and devices in the telemedicine session.

While the above data is being collected, a medical professional who is handling one of the scanning devices or another participant may wish to send audio messages and commentary to other remote participants in the telemedicine session. For example, a technician who is handling an ultrasonic probe may wish to ask a remote specialist whether the probe is properly being applied to the patient, or to comment on an anomaly he or she noticed in the medical images. In some implementations, the participant speaks into a microphone 208 to create the message. The audio message is then transmitted to and received by the patient telemedicine device 104 (step 608).

As previously discussed in connection with FIGS. 2 and 3, the above data and media is selectively transmitted in (near) real time to remote specialists and other participants (e.g., specialist telemedicine device 108). Upon viewing the images and the diagnostic procedure in real time, a specialist may wish to provide audio commentary or requests, annotate some of the received images, or suggest use cases, reference imagery or other resources. Such collaboration data is transmitted from the specialist telemedicine device(s) 108/110, received, rendered and/or displayed in (near) real time at the patient telemedicine device 104 (step 610).

In various designs, an operator of the patient telemedicine device 104 obtains supplementary data (e.g., use cases, reference imagery, medical records, etc.) from a cloud-based server or database (step 612). Additionally, in various implementations, the operator of the patient telemedicine device 104 annotates or marks any displayed images, waveforms or data (step 614). Any of steps 602, 604, 606, 608, 610, 612 and 614 may be performed using any of the techniques and features previously discussed in connection with FIGS. 2 and 3.

Some designs involve storing any of the above received data for later reference (step 616). Such data can be stored in any suitable storage medium e.g., a flash drive, a hard drive, a connected or remote database, etc. The operator of the patient telemedicine device 104 can provide input to the device, causing the device to obtain and display any stored data.

One or more of the received data streams (e.g., biometric images, biometric data, collaboration data, supplementary data, biometric waveforms, video, etc.) are selectively rendered and displayed in real-time at the display device 210 (step 620). At any time, the operator of the patient telemedicine device 104 can configure the device 104 to remove data from the display, to add data to the display, or otherwise arrange the displayed media (step 618). For example, biometric waveforms, patient records, biometric images, video and supplementary data can be presented in separate, resizable and movable windows, as shown in the user interface 400 of FIG. 4.

At almost any time, the operator of the patient telemedicine device can determine data sharing preferences. In some embodiments, the operator of the patient telemedicine device provides input to the device, indicating what kinds of data (e.g., biometric imaging, biometric data, audio, video, collaboration data, supplementary data, etc.) should be shared and what telemedicine devices and professionals should receive the data (step 622). By way of example, an operator could indicate that all biometric imaging, waveform and biometric data received from the medical imaging/sensing devices should be shared with all other participants (e.g., specialist telemedicine devices) in a telemedicine session, but that any annotations and selected medical records only be shown locally at the display device 210.

Generally, the data to be shared is progressively encoded, encrypted and transmitted as it is received or created. In various embodiments, these steps are performed by a data encoding module 800, which is stored at the patient telemedicine device 104.

Figure 8:
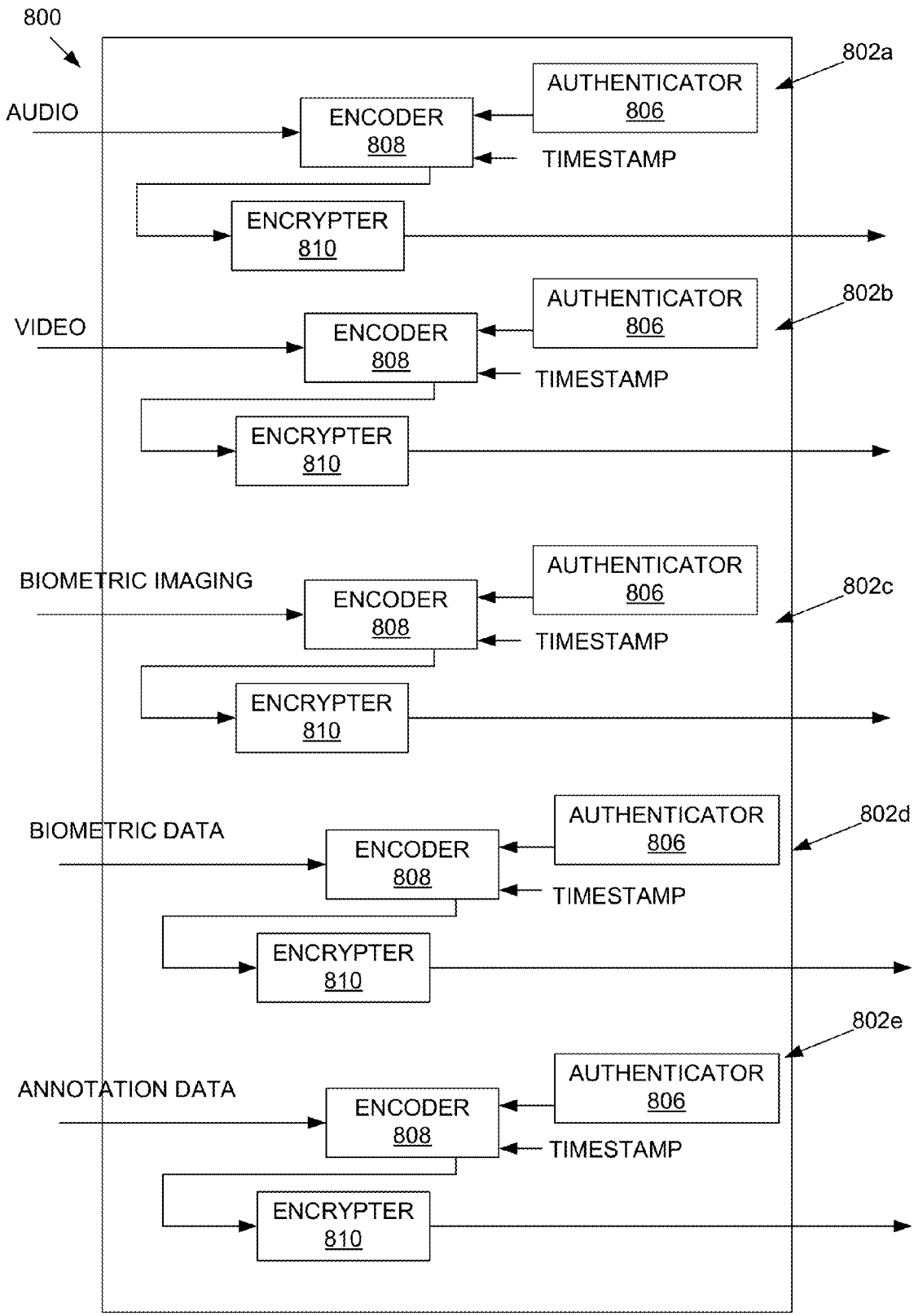
FIG. 8 is a data encoding module according to a particular embodiment of the present invention.

The data encoding module 800 is any software or hardware that is suitable for encoding and/or encrypting data streams. An example of a data encoding module 800 is illustrated in FIG. 8. The data encoding module 800 is arranged to receive multiple, different types of data streams from medical imaging/sensing devices and to separately encode and process the data streams into packet sequences. In the illustrated embodiment, the module receives audio data, video data, biometric imaging data, biometric data and annotation data, although any of the aforementioned data streams received by the patient telemedicine device 104 may also be processed using the data encoding module.

The data encoding module 800 includes multiple submodules 802a-802e that separately process each data type in parallel. That is, submodules 802a-802e receive and process an audio data stream, video data stream, biometric imaging stream, biometric data and annotation data, respectively. Each submodule includes an authenticator 806, an encoder 808 and an encrypter 810. The authenticator 806 helps ensure that only authorized users are able to direct the encoding process and obtain access to the received data streams. The encoder 808 processes, compresses and/or encodes the associated data stream. The encoder 808 outputs frames obtained from the associated data stream. The encrypter 810 is arranged to at least partially encrypt some or all of the frames. The functionality of these various components will be discussed in greater detail below in the context of method 600 of FIGS. 6 and 7.

Returning to method 600 of FIGS. 6 and 7, the data encoding module 800 separately encodes each type of data. The encoding process involves several operations. Frames are obtained from each associated data stream. In various embodiments, frames are provided by an external device (e.g., a medical imaging/sensing device). In some embodiments, a data stream is received and frames are encoded from the data. A frame is a segment, packet or amount of data of any suitable size. In various embodiments, a frame of a video stream or a biometric imaging stream includes an image, although this is not a requirement. At step 623, each encoder 808 compresses (if appropriate) the frames of its associated data stream. Typically, different data streams will be compressed to different degrees, depending on the use and nature of the data. For example, a video stream of a medical professional's face is not a high priority, does not require exceptionally high resolution and can be easily compressed using a wide variety of compression schemes. On the other hand, an ultrasound image tends to have large amounts of noise, which makes compression somewhat more difficult. Additionally, it is generally desirable that transmitted ultrasound images retain a high resolution to facilitate review and diagnosis. Thus, ultrasound images tend to have lower compression ratios than some types of video. In some embodiments, ultrasound image streams are compressed at a ratio of approximately 1:40 to 1:90, while video is compressed at a ratio of approximately 1:250 to 1:1000, although higher and lower compression levels may also be used for particular applications.

In some embodiments, the level and type of compression for some data streams (e.g., biometric imaging streams, such as ultrasound images) is determined dynamically. That is, feedback is received from one or more quality of service agents. The compression scheme used on the data stream is based at least in part on this feedback. Various techniques and arrangements relating to such compression schemes are described in U.S. patent application Ser. No. 14/291,567, entitled "Dynamic Adjustment of Image Compression for High Resolution Live Medical Image Sharing," which is incorporated herein by reference. Any method, component, system, operation or arrangement described in this application may be used to compress a suitable biometric imaging stream or other data stream in step 623.

At step 624, the encoder 808 adds a timestamp to each frame. In various implementations, this timestamp is inserted into a header of the frame. Generally, the timestamp represents an approximate time at which the frame was processed, generated or received at a local device (e.g., the patient telemedicine device 104.) The timestamp can involve any time, value or code that helps indicate time, timing or an order in which frames should be rendered. The timestamp is used to help ensure that frames of particular data streams that are reconstructed at a remote device are properly synchronized and coordinated, as will be discussed in greater detail below. The timestamp may be derived from any suitable source. In some implementations in which the two synchronized streams are received and encoded at the same computing device (e.g., the patient telemedicine device 104), the timestamp can be based on a timer, clock or CPU clock of the computing device. Alternatively, the timestamp can be based on a time received through the network e.g., using the Network Time Protocol (NTP), from a NTP time server or other type of time server, etc. In some applications, the timestamp is based on time data in a GPS signal received from a GPS satellite. These network- or GPS-based approaches work well when synchronization is required between two data streams that originated from different locations or computers in a network.

At step 636 of FIG. 7, the encrypter 810 in each submodule receives the associated frames from the encoder and at least partially encrypts them. Any known encryption technology may be used. In various embodiments, frames from different types of data streams are separately encrypted using different encryption techniques, depending on the characteristics of the data.

Figure 9A:
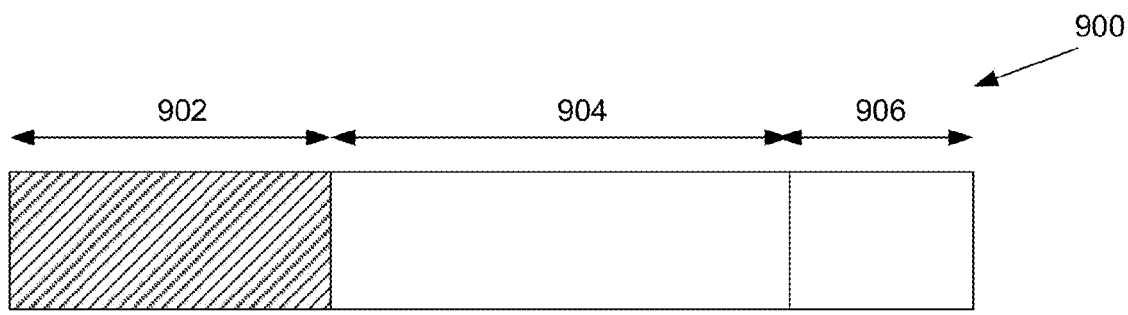
FIGS. 9A-9D are block diagrams illustrating possible encryption schemes for frames according to various embodiments of the present invention.
Figure 9B:
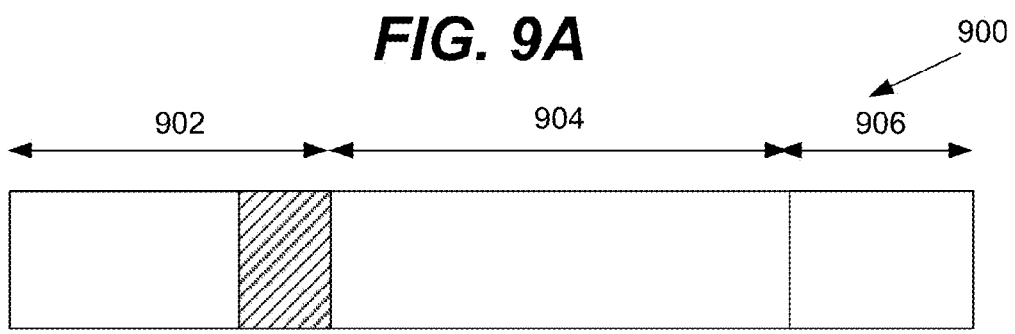
Figure 9C:
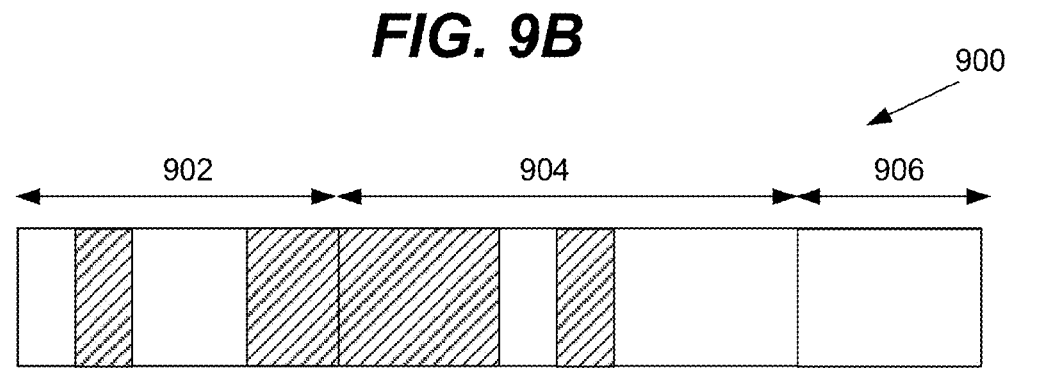
Figure 9D:
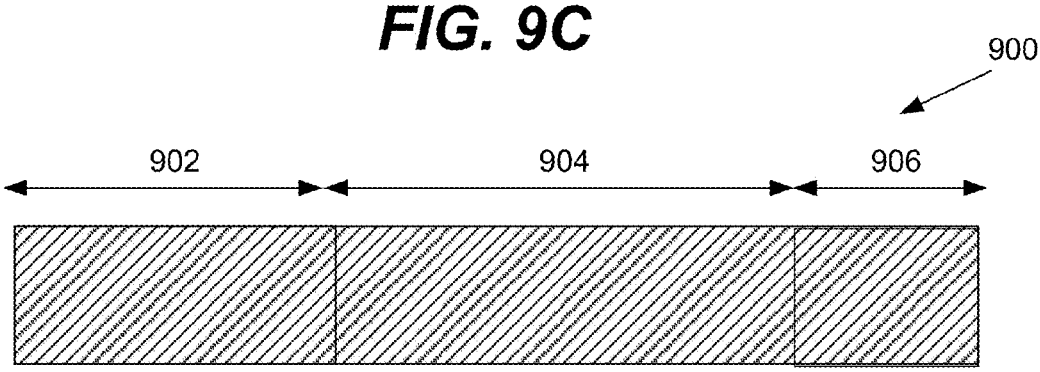

Various encryption operations are illustrated in FIGS. 9A-9D. FIGS. 9A-9D illustrate frames 900. Each frame includes a header 902 and media data/payload 904. The media payload 904 contains a particular media type (e.g., audio, video, biometric imagery, biometric data, etc.) The header 902 includes metadata relating to the media in the media payload 904 of the frame. In various embodiments, for example, the header 902 indicates characteristics of the media payload 904 and/or includes information on how to access, process and/or render the media data. The shaded regions represent parts of the frames that are encrypted, while the white areas of the frames are unencrypted parts. Thus, in FIG. 9A, only the entire header 902 is encrypted. In FIG. 9B, only a portion but not all of the header is encrypted. In FIG. 9C, a portion of the header 902 and a portion of the payload 904 of the frame is encrypted. In FIG. 9D, the entire frame or almost the entire frame is encrypted. In some embodiments, only a particular type of frame is encrypted while other types of frames are not encrypted.

The advantage in encrypting only a portion of a frame or particular types of frames is that it substantially reduces overhead. In various applications, selected portions of each frame are encrypted (and the other portions are left unencrypted) such that an interceptor of the frame would not be able to make sense of the contents of the frame without decrypting those selected portions. The encrypted portion can thus vary depending on the data type and packet structure. That is, video frames may be encrypted in a different manner than biometric imaging frames, etc.

The type of data that is encrypted in each frame can vary, depending on the type of data and the needs of a particular application. By way of example, for multichannel data streams (e.g., from a medical sensing device, such as an electrocardiogram device, electroencephalography device, a pulse oximeter device, a thermal/temperature sensor, a blood pressure testing device, a glucose level testing device, a pulmonary function testing device, etc.), the encrypted portion(s) of a header may indicate a channel ID and/or sampling rate. For biometric imaging streams or video, the encrypted portion(s) of a header of each frame can indicate a number of macroblocks in a portion of the frame, a quantization table, and/or a DC coefficient of each of the macroblocks. In other approaches, a particular type of frame (e.g., an I-, P- or B-frame for video streams) is encrypted and another type of frame is left unencrypted. In still other embodiments, the media payload of a biometric imaging or video frame contains an image, which is divided into multiple slices. Each slice has a header, which is encrypted, although the slices themselves are not. These types of encryption (where some part—but not all—of an image or image stream is encrypted) are sometimes referred to as partial encryption.

Another type of selective encryption is arranged to encrypt a portion of each image data block. For example, consider image or video data that utilizes 8 bit (1 byte) data. Instead of encrypting all 8 bits of each data byte, a subset of the bits can be encrypted. For example, encrypting only two bits out of each data byte would reduce the processing power required for encryption to the order of 25% of the processing power that would be required to encrypt all of the data. Such encryption will visually distort the data sufficiently that it is not useful to unauthorized recipients. The encryption overhead for such an encryption scheme is only a few percent of the compression overhead (i.e., less than 2% for encoding and less than 5% for decoding). Another advantage of such an approach is that the data bit rate remains unchanged and the encrypted data can be treated as a standard video stream for most purposes. Of course, such selective encryption can be integrated with other types of partial encryption as well.

Returning to FIG. 7, after the encryption operations, the data stream encoding module breaks the frames from the various data types down into packet sequences, multiplexes the packet sequences and transmits them (step 638) to a remote device (e.g., to a telemedicine device 108/110). The transmission may be performed using any suitable network protocol, such as UDP or TCP/IP. If a server 116 is available in the multi-site data sharing platform, all traffic may pass first through one or more servers, and then be broadcasted to any participating specialist telemedicine devices from the server(s). Alternatively, the packet sequences may be sent to a single or multiple telemedicine devices directly. In various embodiments, when frames with a particular type of encryption are to be sent, an encrypted message is transmitted to the server or the remote devices, which indicates what portions of each frame are encrypted. This allows an appropriately authorized device at the receiving end to access the frames that follow the encrypted message.

Once the packet sequences are received at the remote device, the remote device reconstructs frames of the various data streams based on the packet sequences (step 640). For example, the biometric imaging packet sequence is used to reconstruct the frames of the biometric imaging stream, the video packet sequence is used to reconstruct the frames of the video stream, and so on. Each reconstructed frame includes a timestamp, as noted in step 624.

For various applications, it is desirable to synchronize frames from two or more data streams. Steps 644, 646 and 648 pertain to the synchronization of different combinations of data streams for different applications. It should be appreciated, however, that any suitable group of different data streams may be synchronized.

Generally, the synchronization of two data streams involves rendering and displaying the frames of the two data streams in order based on their associated timestamps. Put another way, the frames are rendered and displayed at the remote device in the order that they were generated or originally received at the patient telemedicine device 104. If a frame of one data stream was received at the patient telemedicine device at the same time as the frame of another data stream, if the frames are properly synchronized, the two frames will be rendered and displayed simultaneously at the remote device as well, since the two frames should have similar or identical timestamps.

Synchronization is desirable for a variety of applications and data stream combinations. Step 644, for example, pertains to the optional synchronization of frames of a video stream and a biometric imaging stream. To illustrate the value of such synchronization, consider an example in which a patient telemedicine medical device 104 receives a video stream and a biometric imaging stream. The video stream pertains to live video footage of a medical professional handling an ultrasound probe or another medical imaging/sensing device. The biometric imaging stream is received from the medical imaging/sensing device that the professional is handling. That is, the actions of the professional directly and immediately affect what is shown in the biometric imaging stream.

In this kind of situation, it would be desirable if a remote specialist participating in a telemedicine session could watch the professional's use of the device and the resulting biometric imagery in real time and provide suggestions on how to position or use the device. This works well only if the remote specialist perceives little or no delay between the use of the device and the resulting biometric imagery. The rendering and display of the frames of the data streams in order based on the associated timestamps helps ensure such synchronization.

Step 646 pertains to the optional synchronization of frames of biometric waveform and biometric imaging streams. Such synchronization is useful in applications where different diagnostic tests are being applied to the same patient and provide different types of information about the same physiological changes. Consider an example in which an ultrasound probe is being applied to a patient and is generating an ultrasound image of the patient's heart. Additionally, a heart rate monitor is applied to the patient, which is continuously monitoring heart activity and outputting a waveform that tracks the heart activity. Particular changes in the activity of the heart (e.g., a sudden burst of palpitations or a seizure) would simultaneously register in both the waveform and the ultrasound imagery that is being received at the patient telemedicine device in (near) real time. The synchronization of the frames of the biometric waveform and biometric imaging streams allows telemedicine participants to view the waveform and images in (near) real time with the correct timing and order.

Step 648 pertains to the optional synchronization of frames of annotation data and the biometric imaging stream. As previously discussed, in various embodiments any operator of a specialist telemedicine device 108/110 or the patient telemedicine device 104 can annotate frames of a displayed biometric image (e.g., an ultrasound image). In some cases, the annotation takes the form of a circle, line, an underline, a highlight or any other suitable mark. Generally, it is desirable that the association between an annotation and the underlying image or frame be preserved, even as the annotation data and imaging data is streamed to different devices. That is, when the annotation data is transmitted to a remote device and re-rendered, it should be rendered simultaneously with the imaging frames to which the annotation was applied.

Such synchronization can be achieved as follows. Each frame of annotation data represents or includes an annotation that was applied to a particular frame of a biometric imaging stream. In step 624, very similar or the same timestamps are added to the annotation frame and the biometric imaging frame that the annotation was applied to. As previously discussed, the frames of the annotation data and biometric imaging stream are used to form packets. The packets are then transmitted and received at a remote device. At the remote device, the packets are used to reconstruct the frames of the annotation data and biometric imaging streams (step 640), which include the aforementioned timestamps. The reconstructed frames of the annotation data and biometric imaging streams are rendered and displayed in the order of their associated timestamps (i.e., since their timestamps are very similar or the same, the annotation and biometric imaging frames are rendered and displayed (approximately) simultaneously.) As a result, an annotation that was applied to a frame of a biometric imaging stream at a local device can be displayed together with the same frame of the biometric imaging stream at a remote device. That is, at the remote device there should be no or minimal delay between the display of the annotation and the frame of biometric imaging to which the annotation was applied.

The aforementioned steps in FIGS. 6-7 are illustrated in a particular order, but it should be appreciated that in various implementations many of the steps are performed simultaneously (e.g., steps 602, 604, 606, 608, 610, 612 and 614 can occur simultaneously) or may be performed in a different order. Although the method 600 is generally performed by a patient telemedicine device 104, many of the steps (e.g., steps 608-638) can also by performed by any specialist telemedicine device 108/110. Although each step involves particular types of operations, these operations may be modified as appropriate using any suitable techniques known to persons of ordinary skill in the art.

Any of the methods (e.g., methods 600 and 700 of FIGS. 6 and 7), processes, actions and techniques (e.g., operations performed by the patient telemedicine device 104 and/or the specialist telemedicine device 108 in connection with any of the figures) described herein may be stored in the form of executable computer code in a tangible computer readable medium (e.g., in a hard drive, a flash drive, any suitable type of computer memory, etc.) In some embodiments, the computer code is stored in at least one memory of a device (e.g., a patient telemedicine device 104 or a specialist telemedicine device 108/110.) The device also includes at least one processor. The computer code, when executed by the at least one processor, causes the device to perform any of the operations described herein.

Analytics

In radiological diagnostics, it can sometimes be very helpful for a radiologist or other medical professional to see and/or review similar use cases and/or related case studies. To help facilitate such review, the Applicant's have proposed a use case library 119 that can be accessed by medical professionals at any time, including during a collaborative session. Very generally, the library contains a number of records, each of which pertains to one or more particular use cases and/or case studies. In radiological application, each use case preferably has one or more images showing the relevant condition and is classified so that the images can be conveniently searched. The images may take the form of still images, imaging or video sequences, or other segments of a stream (e.g. the output of an EKG machine) and/or cine-loops.

To facilitate searching, the use case records are preferably classified. A variety of different types of tags, meta-data, database fields and/or other markers may be associated with the image to facilitate classification and searching. During classification a significant amount of meta-data is generated about the images. Such meta-data may include a wide variety of different pixel based population features and geometric features corresponding to the image. Such meta-data is associated with the radiological image records to facilitate associative image searching.

The record preferably also includes tags or other information that can further facilitate searching. For example, relevant tags can include items such as: (a) an identification of the imaged organ or body part; (b) a diagnosis or diagnosed condition or other significant diagnostic attributes of the feature(s) of interest (e.g., location, size, appearance, stage, severity, etc. of a growth or lesion); and (c) significant demographic and/or physical attributes of the patient (e.g., age, gender, weight, size, known genetic markers, etc., and in veterinarian applications, species, breed, etc.). Of course, the specific attributes recorded can include any attribute(s) that are considered relevant to the particular condition. Generally, the more detailed the recorded attributes are, the better the more pertinent the search results tend to be.

To give a specific example, consider a veterinarian application in which an ultrasound exam is being conducted on an 8-year old German Sheppard dog. While observing the ultrasound in real time, the radiologist identifies a feature of concern in the ultrasound scan. The radiologist can mark the feature or region of concern/interest on the image and initiate a search of the use case library for similar images. Meta-data about the marked region of the image is used in an associative pattern search and patient and/or image related information can be used to help narrow the search results to a set of results that are perceived to be the most pertinent to the issue at hand.

The search results identify similar types of images in the use case library which can be helpful in making or confirming a diagnosis. The search results can also be helpful in developing a recommended treatment plan since the records in the use case library may include case studies that describe treatment plans and results for the conditions illustrated in the images in similar types of patients (e.g., a similar occurrence, preferably in a similar aged dog of the same breed and size).

Figure 10:
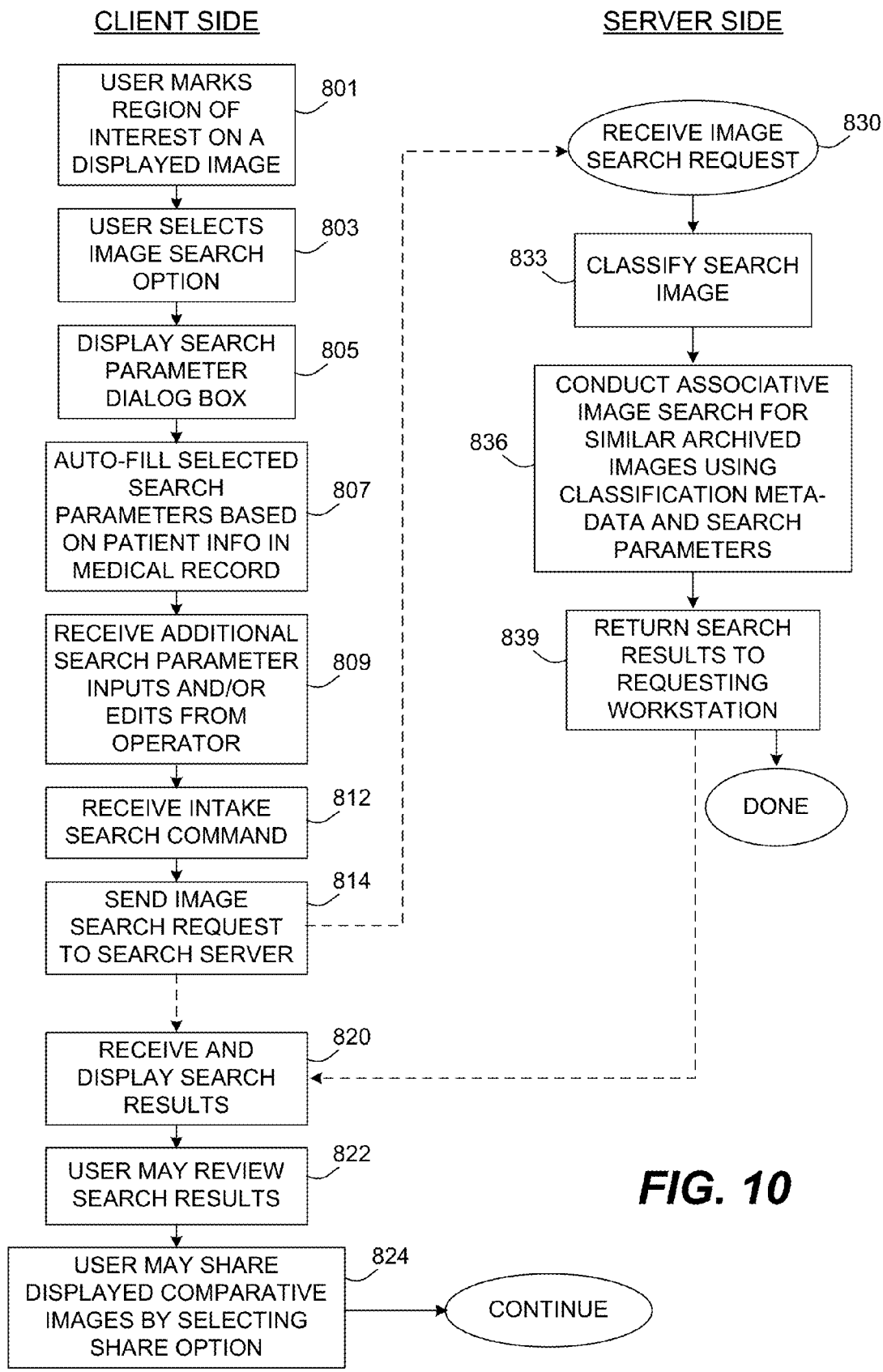
FIG. 10 is a flow chart illustrating a method of searching for a comparative image in accordance with a described embodiment.
Figure 11:
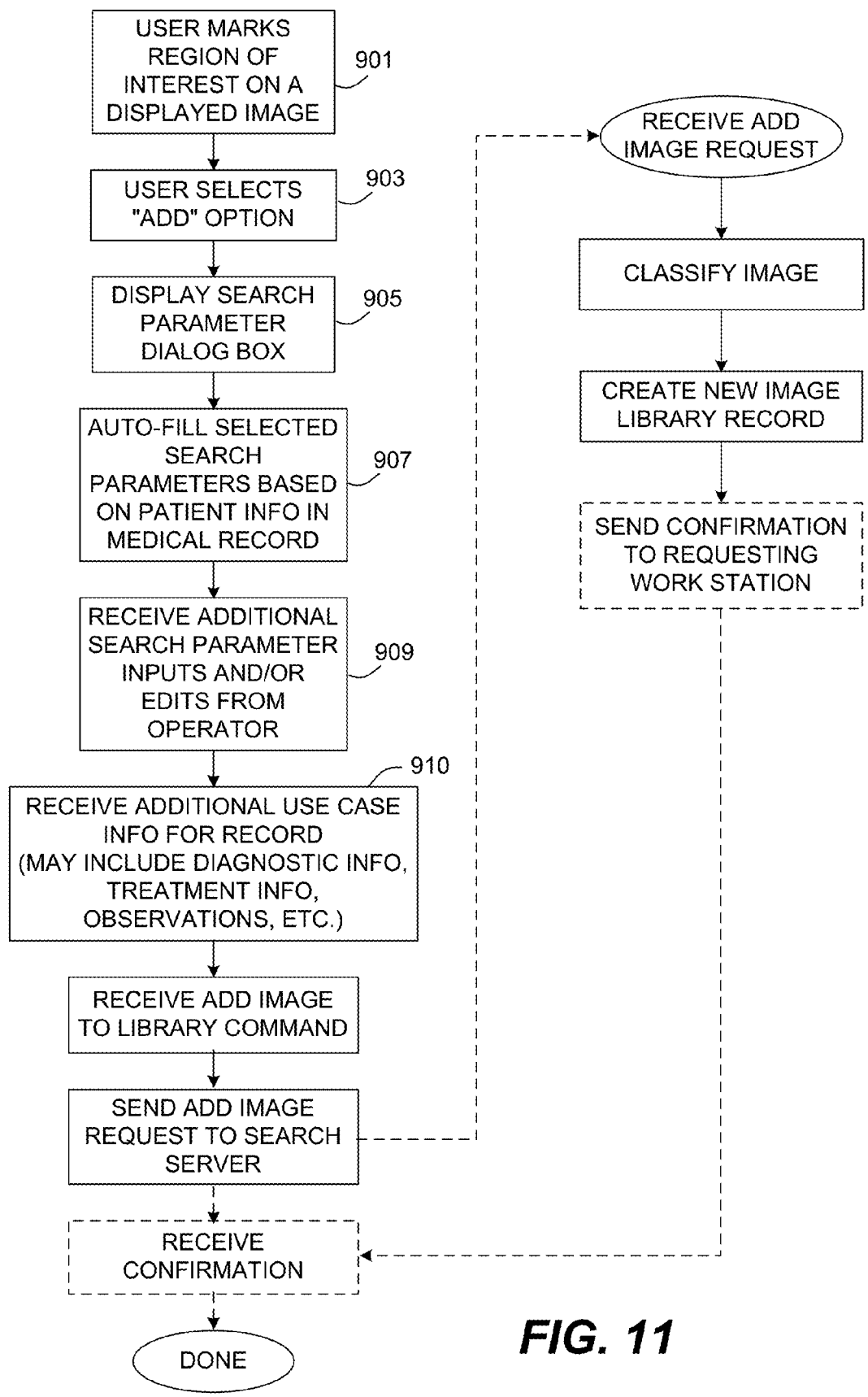
FIG. 11 is a flow chart illustrating a method of adding an image record to a medical image library in accordance with a described embodiment.

Referring next to FIGS. 10-11, a representative use scenario for the analytics module will be described. Although a particular use scenario is described for illustrative purposes, it should be appreciated that the described search capabilities can be initiated from a wide variety of different locations and can be utilized in a wide variety of other applications.

In the illustrated scenario, a user sees an area of interest in a sonographic stream. The image is frozen at the desired location (which may be accomplished by selecting a pause button during either a live session or a replay session or through any other appropriate mechanism). The user then marks the region of interest. This may be accomplished by drawing bounding box around the region of interest or using any other suitable approach. The user then requests a search for similar images. The search request initiates a search dialog box that is displayed in an analytics window. If an analytics window/view is already open, the search dialog box is displayed in the open window/view. If an analytics window/view is not already open, a new window/view is opened to display the dialog box. Of course, the dialog box can be displayed in any other suitable manner, and is some alternatively embodiments, the search dialog box can be eliminated.

The search dialog box allows the user to input relevant search parameters. A very wide variety of search parameters are possible. By way of example, relevant search parameters may include various patient attributes, the organ or body part of interest, the location of interest on the organ/body part and various attributes descriptive of the feature of interest. In some embodiments, auto-fill is used to populate relevant fields that can be drawn from the patient's medical record. For example, in veterinarian applications certain patient attributes such as species (e.g. dog), breed (e.g. German Sheppard), gender, age, weight etc. can typically be drawn from the medical record and auto-filled. There may also be relevant items from the patient's medical history (e.g., the patient previously was diagnosed with a particular type of cancer, etc.). In our example, the radiologist may manually enter search parameters that are not auto-filled, and delete any auto-filled parameters that are not desired. In this case, the radiologist might enter liver as the relevant organ/body part, as the location, and describe the lesion. When the radiologist is satisfied with the search parameters, the search may be initiated by clicking search button, or using any other appropriate interface.

When the search is initiated, a search request including all of the entered search parameters is sent to server 116 together with a search image. The search image includes at least the portion of the image that has been marked. Depending on the nature of the associative search algorithm used, it may be desirable to send only the portion of the image that has been marked as the search image, or a larger segment of the image, up to and including the entire image frame. In some circumstances it may even be desirable to send a short image sequence as the "search image." When a larger segment of an image is sent, as the search image, an indication of the bounding box or other markings that identify the relevant portion of the image is also sent to inform the classifier of the most relevant portion of the image.

The server performs an associative search on the search image and uses the received search parameters to help refine the search and/or search results. The search results are then returned to the requesting workstation/device—where they are displayed in analytics window. The operator may then select any of the use cases identified in the search results for review—with the selected item being displayed in the analytics window.

Most often, the image segment of interest (search image) will be sent to the server 116, which classifies the image segment appropriately for the associative search. However, in alternative embodiments, such image processing can be done at the client side (i.e., at the requesting workstation) and the resulting meta-data about the image can be sent to the search server in addition to or in place of the image file.

Although a particular graphical user interface is illustrated for initiating search requests and displaying search results, it should be appreciated that a wide variety of other search input and search result display interfaces may be used.

To facilitate an associative search, both the library images and images to be searched must be classified. There are a wide variety of known types of classifiers that can be used to classify records for the library. These include both supervised and unsupervised classifiers. By way of example, supervised classifier may include, but are not limited to classifiers such as: Rule based classifiers; N/i classifiers; Bayesian classifiers; Linear Discriminant/Perceptron classifiers; Artificial Neural Networks (ANN); Support Vector Machines (SVM); and Hybrid rule-based & statistical classifiers. Unsupervised classifiers may include, but are not limited to classifiers such as: Natural Grouping classifiers; k-Means clasifiers; and Kohonen nets.

As will be appreciated by those skilled in the associative search arts, each type of classifier requires its own processing of the images and the particular features analyzed by any particular classifier may be widely varied. Very generally, the features analyzed may include pixel based population features of the image, geometric features of the image and/or any other feature of the image that is of interest to a particular classifier.

The illustrated embodiment is arranged such that any authorized user may add a use case to a library of interest or even create their own use case library. For example, a radiologist that sees an image that is believed to be worth adding to the use case library 119 can mark the region of interest in substantially the same way described above for searching. However, instead of selecting "search", the radiologist selects "add" to add an image to the use case library. In this case an add dialog box is displayed in the analytics window. Like the search dialog box, the add dialog box allows the use case record creator to input various relevant attributes about the patient, and to describe various features of the image that might be useful in classifying, searching or interpreting the image. Again, such items might include the organ or body part of interest, various diagnostic attributes of the image of interest such as any diagnosis, the location of the feature of interest on the organ/body part and various attributes descriptive of the feature of interest. In some embodiments, auto-fill is used to populate relevant fields that can be drawn from the patient's medical record. While information may be drawn from a medical record, for patient privacy purposes, it is strongly preferred that the use case records in any human use case library not include any information or images that can be used to identify a specific patient. Rather, patient information is preferably limited to general demographic and physical data and relevant medical descriptions.

The use case record creation facility also preferably allows the creator to add other comments and/or descriptions to a record that might be helpful to a practitioner that views that record in the future. Such additional information might include comments about the image, patient symptoms, information about treatment plans that are proposed, or have been followed, and/or any other information that may be helpful to reviewers in the future.

As discussed above, any view displayed on a user interface may be annotated and/or shared. To facilitate sharing, each window or pane may include a set of control tabs that may be activated by a user clicking on the tab. In the analytics view, one of the tabs is a "share" tab. When a share tab is selected, the information presented in the analytics window (e.g. a reference image selected from the result of an associative image search, with or without annotations) is shared with other workstations as previously described.

Replay

There are times when a user may want to review a portion of a session for diagnostic, educational or other reasons. To facilitate this, each biometric stream is preferably stored as a video file, at least temporarily at each workstation (e.g. in workstation memory or storage 109). The user interface 1000 includes mechanisms that allow a user to replay a recorded session and/or to capture segments of the session to be reviewed, shared with others, archived, etc. Representative user interfaces that may be used to facilitate such mechanism are described below with reference to FIGS. 12-17.

Figure 12:
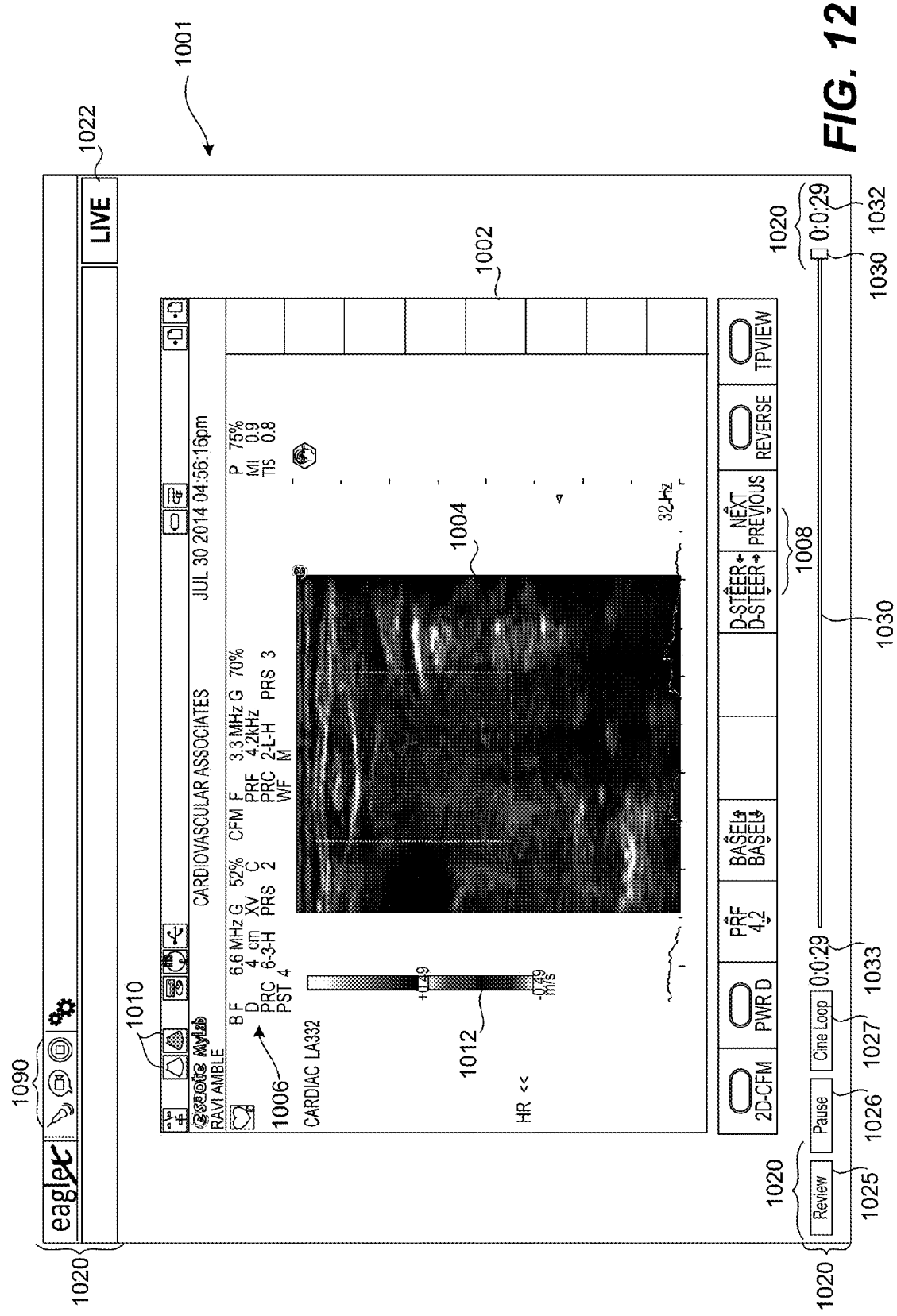
FIG. 12 is a representative screen shot of a window displaying a live ultrasonic imaging session and the accompanying user interface in accordance with one described embodiment.

FIG. 12 illustrates a user interface for displaying a live ultrasonic imaging session in accordance with one embodiment of the invention. In the illustrated embodiment, window 1001 has an imaging session frame 1002 that displays the same images that are seen on the ultrasonic imaging machine's display screen. This includes the ultrasonic image 1004 itself, together with all text 1006, control buttons 1008, icons 1010, graphics 1012, etc. that are displayed on the ultrasonic imaging machine's display screen. Although the view could be simplified by only presenting the ultrasonic image 1004 itself, it is preferable to present all of the imagery and text displayed on the ultrasonic imaging machine's display screen so that the collaborating specialist can see the ultrasonic imagining machines settings, etc., just as they are seen by the technician conducting the examination. The accompanying information will vary based on the imaging machine in use—but, by way of example, may include information such as the ultrasonic frequency(ies) in use, image focus depth, etc.

The user interface 1000 also includes regions 1020 outside of the imaging session frame 1002 that present information and provide control interfaces that are relevant to the current view. In the embodiment illustrated, these include a status indicator 1022 that indicates the nature or mode of the current view; a plurality of control buttons 1025, 1026, 1027 that permit the user to select other available display modes in the current view and/or control features available in the current view; a scroll bar 1030 that shows the currently displayed location in the session; and session controls 1090 that permit the user to control other aspects of the collaborative session.

There are a number of display modes that are available for the imaging session. The available modes may include a "live" mode which displays the images from the current ultrasonic imaging session in real time; a "review" mode that allows a user to replay the current session; and a segment capture mode which allows the user to isolate segments of the current session that are of particular interest. Of course other discrete modes may be provided as well as desired.

Figure 13:
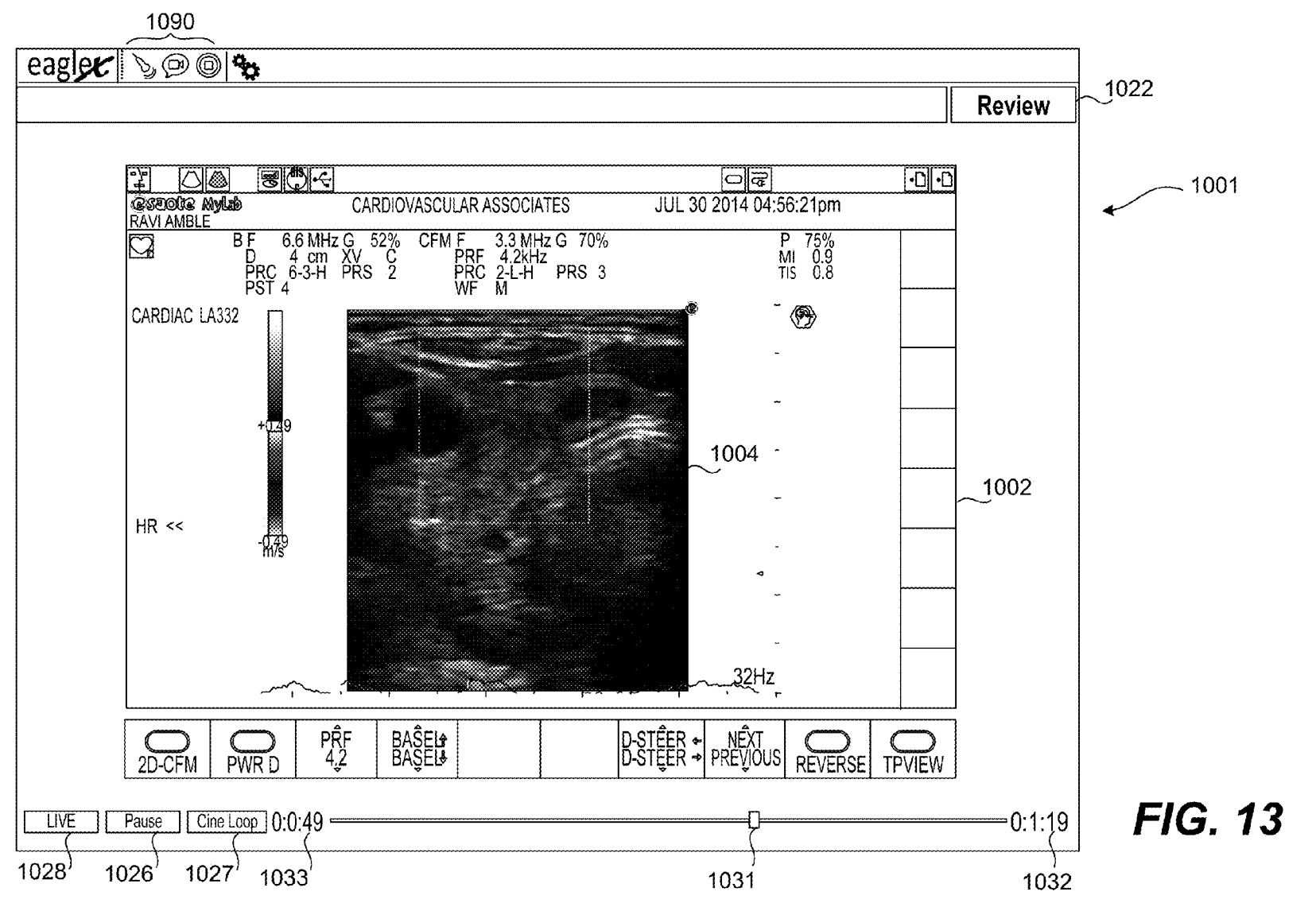
Figure 14:
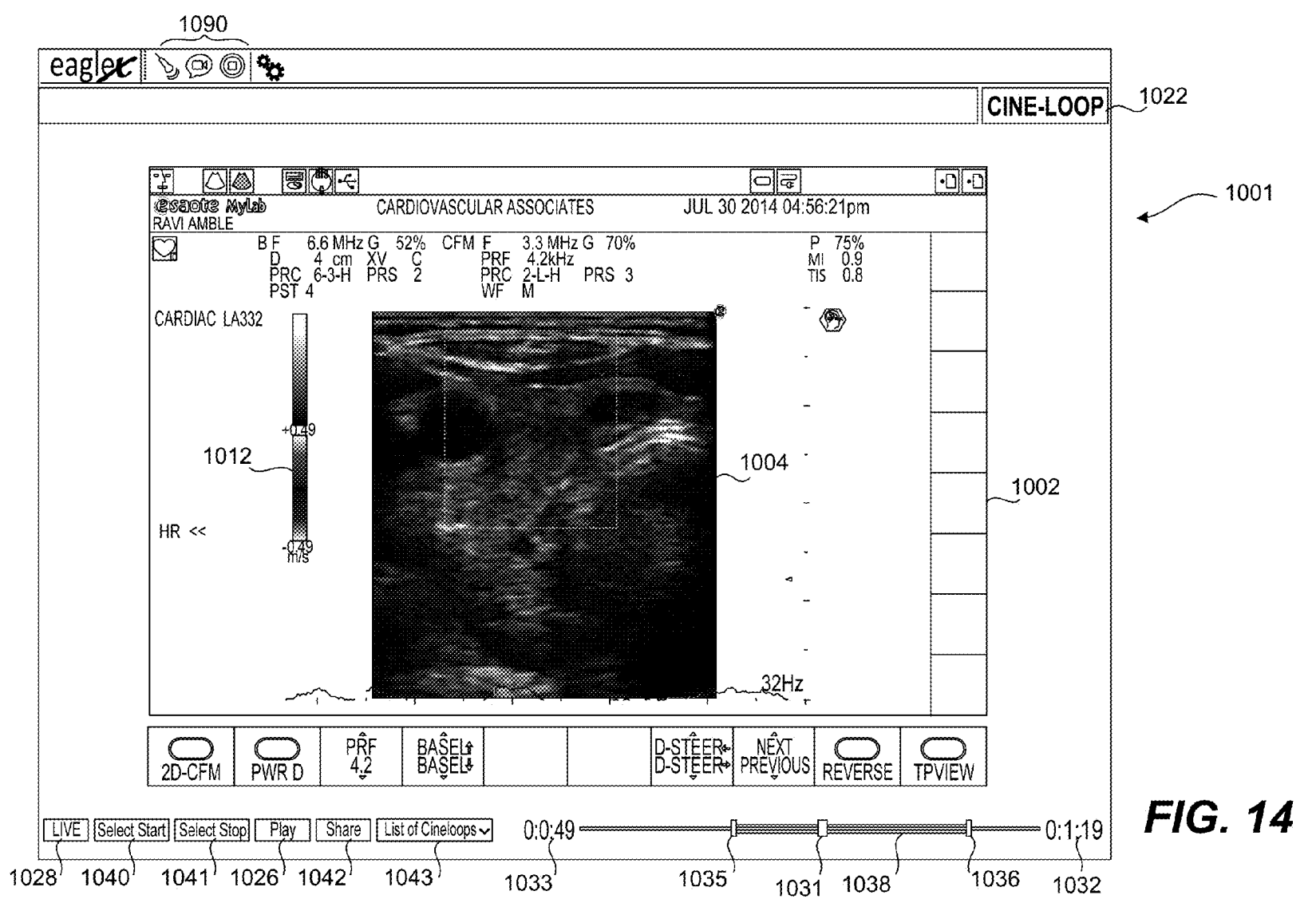

The view illustrated in FIG. 12 is a live imaging stream so the status indicator 1022 indicates that the session is in a "LIVE" mode. In contrast, if the view presented is a replay of the current session, then the status indicator 1022 might indicate "REVIEW" as illustrated in FIG. 13, or if the view presented allows a user to isolate a segment of the session then the status indicator 1022 might indicate "CINE-LOOP" as indicated in FIG. 14. Of course the specific indicators (e.g., text, labels, graphic images, icons, etc.) used in status indicator 1022 to identify the various modes may be widely varied and are in no way limited to the specific indicators that are illustrated.

Control buttons 1025, 1026 and 1027 allow the user to select other display modes that are available in the current view and/or control the current view. By way of example, in the live view illustrated in FIG. 12, the control buttons include review button 1025, stop/start button 1026 and cine-loop button 1027. Selection of review button 1025 transitions the view to the replay mode as illustrated in FIG. 13. Selection of start/stop button 1026 pauses the displayed stream at the current image. When a pause occurs, the start/stop button 1026 may display a suitable indicator such as "start" or "play" and subsequent selection of the start/stop button returns the view to the live view. If the user wishes to view the portion of the imaging session that was viewed while the display was paused, they may review that portion of the session in the review mode. Of course, in other embodiments, the user interface could be arranged to continue displaying the image stream from the paused location in the review mode after pausing a displayed image or separate control buttons may be provided to allow the user to select either "return to live" or "continue from pause." Selection of cine-loop button 1027 transitions the view to the segment isolation mode as illustrated in FIG. 14.

The scroll bar 1030 within control region 1020 has a slider 1031 that graphically shows the location of the displayed image within the imaging session. Timer 1032 displays the total time of the current imaging session (i.e., the total time that the ultrasonic imaging machine has been active in the current session). Timer display 1033 shows the location of the currently displayed image in the session. As would be expected, in the live session, the current display time is the same as the total session time since the session is being viewed live. In the live mode the slider 1031 within scroll bar 1030 may optionally be disabled so that the user must affirmatively select the review mode to view anything other than the live imagine stream.

When the review mode is selected (e.g. by selecting review button 1025), the view within frame 1002 transitions to a review view and the various icons and other information displayed in control region 1020 is changed to the control features and information suitable for display in the review mode. One such representative view is illustrated in FIG. 13. In this view, the status indicator 1022 now shows that the view is currently in the review mode. The available control buttons have changed to include start/stop button 1026, cine-loop button 1027 and live button 1028. The selection of the live button 1028 returns the view within frame 1002 to displaying the live ultrasound stream in real time as illustrated in FIG. 12.

The replay mode view preferably includes user interface controls that allow a user to quickly navigate the stored stream to a desired location. Such controls may include typical GUI control mechanisms such as play, slow play, pause, a navigational scroll bar, fast forward, rewind (fast backward), and/or any other suitable mechanism that facilitates navigation of the stored video file. When the image is paused (in any of the various modes) a "next" image control button can be displayed that permits the user to index to the next image frame in the stream. Similarly a "previous" button can be provided to permit the user to index back to the immediately previous image frame in the stream. This type of frame by frame image control is particularly useful in permitting a user to identify the best available image frame for showing a desired feature.

Optionally, the user interface may be configured to immediately start replaying the video file, or a preselected portion of the video file when the replay mode is entered. Since the entire session is stored locally, any portion of the current ultrasonic imaging session stream may be replayed substantially immediately at the user's request.

In the embodiment of FIG. 13, the navigational tools include scroll bar 1030. The slider 1031 on scroll bar 1030 provides a mechanism that allows the user to access any portion of the stream in a conventional manner (e.g., by dragging the slider 1031 to the desired location within the stream). In the replay view, the timer display 1033 again shows the location of the currently displayed image within the session—which would often be some intermediate portion of the session as illustrated. In some implementations it may be desirable to limit the portion of the session that is available in the replay mode to the portion of a live session that occurred before the replay mode is entered. In such embodiments, timer 1032 may optionally be arranged to display the total time of the "replay" session—i.e., the total time of the portion of the session that is currently available for display in the replay mode. A potential advantage of this approach is that it may be easier for users to navigate using the slider when the length of the session being reviewed doesn't change dynamically during the review cycle. In other implementations, the timer may continue to show the progress of the session.

The replayed imaging stream may be paused at any location by selecting the start/stop button 1026. When paused in the review mode, the text or image displayed on the start/stop button 1026 may be changed to indicate that selection of the button will resume the replay (e.g., "start" or "play" or a suitable graphic image). It is noted that in the replay mode, the frame 1002 still displays the entire screen view from the ultrasonic imaging machine. This again gives the reviewer context as to the machine settings, etc. that were being used to obtain the displayed image.

The user interface also has a mechanism for selecting specific segments of a biometric stream or video file. For example, if an ultrasonic imaging session extends for 15 minutes, it may be desirable to isolate a shorter segment of that session that focuses on a specific area of interest or concern. The isolated segment of interest may be a single frame/image, a sequence of frames/images, a short video clip or any other segment of the video file. When the stream is stored locally as a video (or other) file, the isolated segment can be characterized or marked simply by identifying the breakpoints (e.g., the start and end points) for the segment within the stream or video file. The breakpoints can be identified in any suitable manner. By way of example, in some implementations, the start point of a segment can be identified by a user clicking on or otherwise selecting a "record" button or equivalent GUI mechanism displayed or otherwise accessible in the relevant view. Selecting the same button a second time can be used to identify the end of the isolated segment— which serves to stop the "recording." Of course, a wide variety of other conventional GUI or other user interface mechanisms may be used to identify the breakpoints. In some implementations, the GUI is arranged to facilitate the creation of more complex segments by allowing a segment of interest to be composed of two or more concatenated segments taken from the imaging session. This can readily be accomplished by enabling "restart" and segment end breakpoints that can be used to identify additional segments from the original stream/video file to be included in an isolated segment of interest.

In embodiments where the stream is stored, there is no need to separately store the "recorded" session. Rather, the segment is uniquely identified by marking its breakpoints (e.g. start and stop points) within the session. As previously described, in one implementation, each frame in a stream has a corresponding timestamp. In such an implementation the start and end points may be identified by simply saving the timestamps associated with the start and stop points. If the stream is marked in a different way, as for example by frame number, the start and stop points can be identified by frame number or in any other suitable way based on the nature of the stream. If a particular workstation is not set up to automatically store the incoming stream(s), the activation of the record function can initiate storage of an incoming stream and the ending of the record session can stop the storage of the incoming stream. Alternatively, if the session is stored at another location (e.g., on a server or at the originating workstation) the timestamps can be used to identify the selected segment which can be retrieved from the remote storage when it is desirable to replay the segment.

It should be apparent that the described "record" functionality can be performed on any imaging stream or biometric monitoring stream or video that is being viewed on the workstation. This includes both the live stream and stored video files that are being replayed in the replay view. If desired, such recording can even be performed on a segment that is being replayed or a file retrieved from storage—although it is expected that such applications will be less common Any stream (live or recorded) can be paused at any point. A pause is accomplished by selecting a pause button (or any other suitable pause mechanism) while a stream is being rendered. Any displayed image can be separately identified by selecting a "save image" button or other suitable record mechanism while the stream is paused. Once again, the timestamp associated with the selected frame may be used to uniquely identify the frame within the video file. Of course, in other implementations, other suitable markers including frame numbers or other indices may be used for the same purpose.

Figure 15:
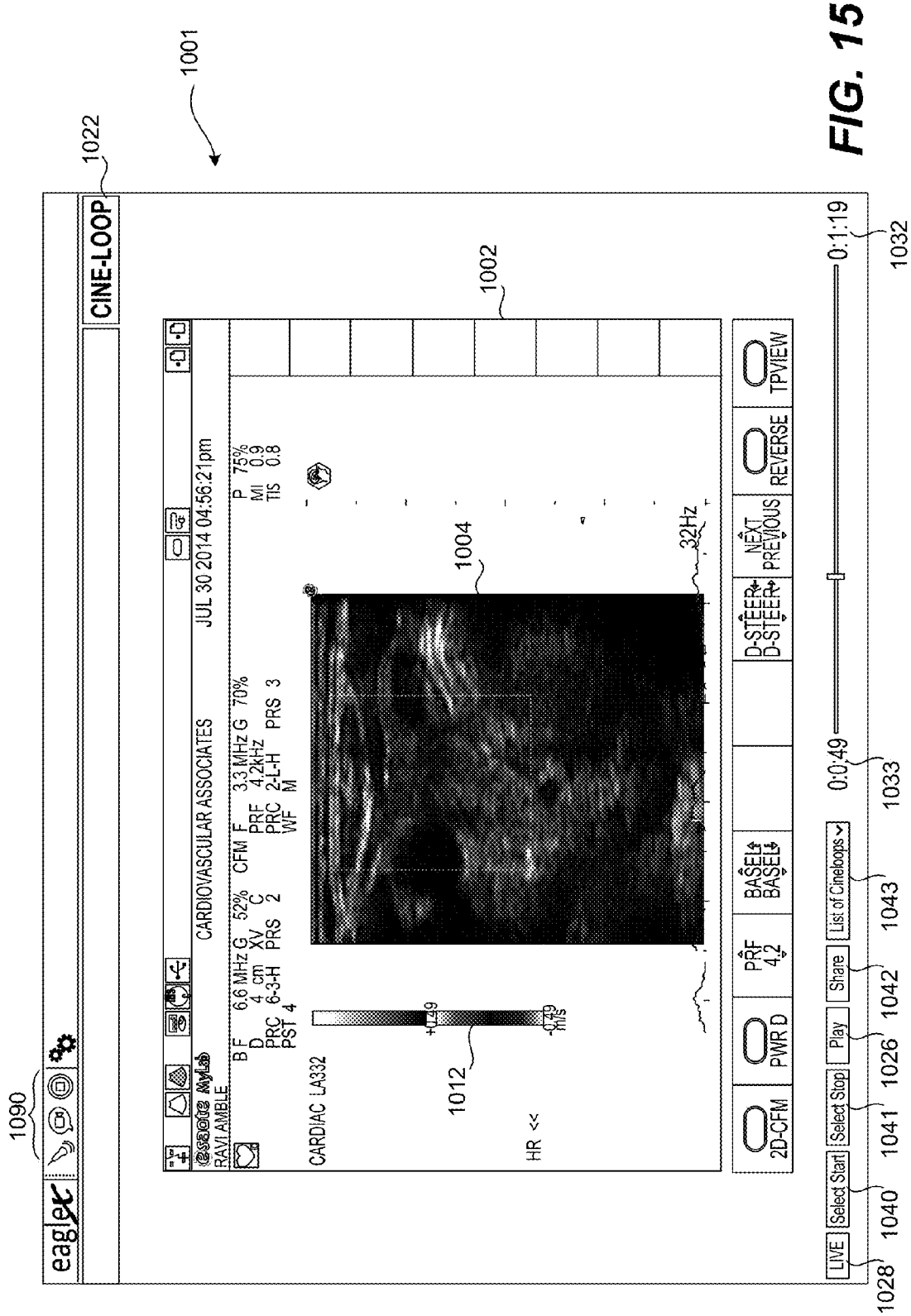
FIG. 15 is a representative screen shot of the window of FIG. 14 poised for the creation of a Cine Loop mode.

In the embodiment described with respect to FIGS. 12-14, selection of the cine-loop button 1027 from any of the other views puts the view in a segment capture mode which allows the user to select a relevant portion of the imaging session to be reviewed, shared with other collaborators, archived, or otherwise utilized. Such segments are sometimes referred to herein as "cine-loops" in part because they are typically rendered as a continuous loop (although that is not a requirement). A representative segment capture mode interface 1055 is illustrated in FIGS. 14 and 15. In this mode, the status indicator 1022 indicates the current mode (labeled "CINE-LOOP" in the drawing) and appropriate mode control button(s) is/are provided to allow the user to transition into any of the available modes. In the illustrated button, only live mode control button 1028 is presented as an option, although in other embodiments, additional buttons or other mechanisms could be provided to switch to other available modes.

The segment capture interface also includes a number of other control widgets that are appropriate to facilitate creation of the cine-loop segments. In the illustrated embodiment, these mechanism include start/stop button 1026, segment begin button 1040, segment end button 1041, share button 1042 and a menu 1043 of the available cine-loops. The start/stop button 1026 and the scroll bar 1030 allow the image stream file as previously discussed. Selection of the segment begin button 1040 marks the location in the imaging stream corresponding beginning of a segment to be created—which may be graphically represented by the display of a begin segment marker 1035 on the scroll bar 1030 as illustrated in FIG. 15. Selection of the segment end button 1041 marks the location in the imaging stream corresponding end of the new segment and may be graphically represented by the display of an end segment marker 1036 on the scroll bar 1030. In the illustrated embodiment, the resulting segment is graphically represented by widen portion 1038 of the scroll bar, which provides context as to the location of the segment.

In some preferred embodiments, the interface allows for multiple segments to be created if desired. Once a segment/cine-loop is created, it may be reviewed by the creator by simply selecting the "play" and "pause" as desired (e.g., start/stop button 1026). When a segment has been created, it is added to a list of segments that are available to the session. In the illustrated embodiment, that list of segments may be displayed in menu format by selecting menu 1043. Any of the identified segments may be selected and the selected segment appropriate controls are then displayed in frame 1002/window 1001. In some embodiments, when a segment is active, a sub-segment of that active segment may be selected using the described tools to create a new segment/cine-loop.

The user interface also includes a "share" mechanism that allows an operator to share the selected segment/cine-loop. Again, the shared segment may be a single image, a sequence of images, a short video clip or any other segment of the video file. After a segment has been identified as described above, the segment of interest may be shared with collaborators by simply selecting a share function. In the illustrated embodiment the share function is activated by selecting share icon 1042 in the segment selection view illustrated in FIG. 14, although it should be appreciated that a wide variety of other alternative interfaces may be used to facilitate the same functionality. Since each workstation preferably stores a copy of the stream, the selected sequence or frame may be shared by simply sending an indication of the starting and stop timestamps to the collaborating workstations. When a workstation receives a shared segment notification, the user interface at the receiving workstation is arranged to notify a user in an appropriate manner. The operator of the collaborating workstations can then open their own replay windows and view the shared segment in the same manner previously described. In some implementations, the replay window is arranged to automatically start playing the shared segment when a shared segment is accepted.

Figure 16:
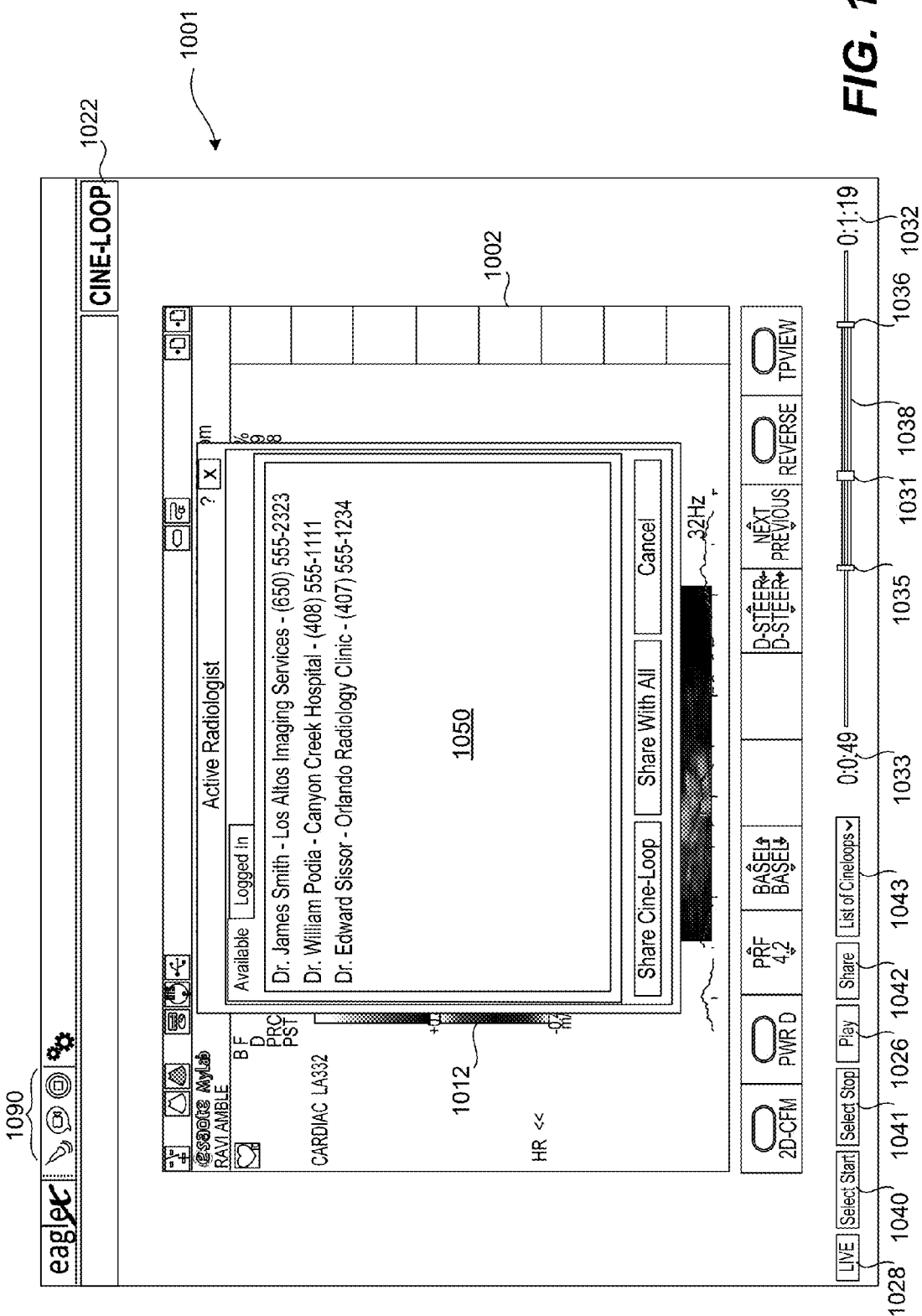
FIG. 16 is a representative screen shot of the window of FIG. 14 showing a dialog box that may be used to facilitate sharing a Cine Loop with collaborators.

In the embodiment illustrated in FIG. 16, selection of the share button 1042 instantiates dialog box 1050 which provides a list of individuals with whom the current segment may be shared. Typically, the list would include each of the other current participants in the tele-medicine session. Depending on the nature of the session, that could include a single other party or multiple other parties. The user can select the desired recipients from the list and transmit the segment to the selected recipients by selecting an appropriate sharing mechanism from the user interface. In the illustrated embodiment, selection of button 1051 causes the segment to be transmitted to each of the selected parties, and selection of button 1052 causes the segment to be transmitted to all of the listed parties. Selection of button 1053 cancels the share function before transmitting the segment to any of the selected or displayed parties.

As previously mentioned, each of the tele-medicine participants will typically have a locally stored version of the imaging session. As described earlier, for such participants, all that needs to be transmitted to "share" the selected segment are the start and end points for the cine-loop within the session and the interface within their own computers can render the appropriate sections. However, in other embodiments, a particular participant or a third party of interest may not have a copy of the entire session. In such circumstances, the video stream that comprises the selected segment can be sent instead of simply the end points. The recipient(s) of the segment may then review the transmitted segment as part of the collaborative session so that the interesting features may be discussed, noted or otherwise handled in real time as appropriate. In still other embodiments, parties that don't have a local copy of the imaging session may access the cine-loop from a remote server. An advantage of this approach is that it reduces the bandwidth load on the sharing workstation.

The ability to share the segment of interest with third parties who may not already be part of the collaborative session is a powerful feature. For example, there are times during a radiology session when a reviewing technician, doctor or radiologist may desire a second opinion concerning a feature that is seen in the radiological stream. In another example, a radiologist may wish to show the results to the patient's physician or surgeon, so that any questions may be answered or a diagnosis reviewed during the imaging session, without requiring physical present of the physician/surgeon. In such circumstances, the person wishing to share a segment of interest can select a person who has a compatible workstation but is not part of the current session to receive the segment. That person may then join the session as participant while the diagnostic session is still in progress so that the second opinion or consultation may be rendered in real time. Although only a few specific examples of third party collaboration have been provided, it should be appreciated that there are many other types of circumstances where it might be desirable for a third parties to be able to see a selected segment of an imaging session while the session remains active. These may include a variety of different educational, consulting, informative or other settings.

In one particular example, a reviewing radiologist may wish to get a second opinion from another expert radiologist. To support such a scenario, the dialog box may be configured to list other radiologist that are currently available for consultation as illustrated in dialog box 1050. The list of available radiologists may come from a central server (not shown) with which radiologists that are available for consultation may register.

When a segment is shared, the recipients of the segment are notified of their receipt of a shared segment and they may then view the segment in their own view. The notification of the receipt of a message may take any suitable form. By way of example, in the embodiment illustrated in FIG. 17, a participant in a tele-medicine session has received a segment (cine-loop) from another participant in the session. In this circumstance, a dialog box 1055 appears in a recipient's current view informing the recipient of the receipt of the segment. The recipient may then accept or decline the received segment by selecting appropriate features (e.g. buttons) in the dialog box.

Once a segment is selected, it may be accessed at any time by entering the Cine-mode (e.g., by selecting Cine Loop button 1027 and then selecting the desired segment form the menu of available segments 1043).

The described sharing functionalities may be utilized in connection with any stream, video file or segment displayed on a workstation. Thus, in addition to selecting and/or sharing of segments of the current imaging or biometric monitoring session, the workstation operator may elect to share reference use cases retrieved from a library or prior images, video segments from the patient's medical file, and/or other similar materials using similar mechanism. Although some particular segment creation, sharing and notification interfaces have been illustrated, it should be understood that a wide variety of other GUI mechanisms may be used to facilitate the same types of control and/or any other control deemed suitable in the segment creation mode.

In the embodiment illustrated above, any of the live, replay or segment creation modes can be selected from a single window or view 801. In other instances, it may be desirable to open a separate window (not shown) to replay a past portion of the session while the session continues. This can be accomplished by opening a new window or pane upon the selection of a replay icon (not shown) in the session controls 890 or at another suitable location in the interface (including review button 825 in an alternative embodiment). Of course, as with all of the previously described views, a wide variety of other user interface actuating mechanisms including pull down menus, tabs, specific gestures etc. can be used to open a new view/window/pane or to transition a particular view to a different mode (e.g., replay mode, segment isolation mode, etc.).

Annotations

A user may also mark or annotate any biometric stream or image displayed on their workstation. This can include the live biometric stream, an image, a sequence, segment or cine-loop taken from the biometric stream, and/or a reference image, sequence, segment or cine-loop (collectively reference materials). The reference materials may be patient specific (e.g. earlier examination results of the same patient which may be stored as part of the patient's record) or can be more general reference materials that are retrieved from a use case library or other suitable source.

To mark a region of the screen, the operator activates an annotation mode in the relevant view. By way of example, the annotation mode is entered by selecting an annotation tab (not shown) in the relevant view. Of course, in alternative embodiments, a wide variety of other conventional GUI controls may be used to activate the annotation mode. In the annotation mode, the user may mark any portion of the view and such markings are recorded. For example, a user may draw an arrow pointing to a region of interest and/or may draw a graphical bounding box that encircles another region of interest. Textual annotations may be entered (e.g. typed) into a text annotation box associated with the marked image(s). The annotation engine saves the annotations together with an indication of the image(s) that the annotations pertain to. For example, if the annotations are made on a still image, the annotation engine would store the annotations themselves, together with the filename and the timestamp associated with the frame of interest. If the annotations are for a stream segment, the annotation engine may indicate the clip that the annotations are associated with. If the annotations are associated with only a portion of a stream or clip, the breakpoints (e.g., start and end points) for the annotations relative to the clip are stored as well so that they may be rendered at the appropriate time.

In practice, many clips are relatively short in nature so that annotations made on the clip will be displayed over the entire duration of the clip. However, that is not a requirement. Thus, if the annotations are only relevant to a portion of the clip—annotation start and/or end points may be used to identify when the annotations are to be displayed. As with the identification of clips themselves, the start and endpoints of the annotations may be based on the frame timestamps (i.e., by indicating the timestamp associated with the beginning of the annotation and/or the timestamp associated with the end of the annotation).

When desired, the annotations may be saved as part of a clip or the stored version of the entire session. Thus, the annotations are available any time that an annotated clip or session is accessed. Similarly, when a selected image or segment has been annotated, the annotations may be transmitted to collaborating workstations together with the segment identifying information any time a segment is shared.

Although only a few embodiments of the invention have been described in detail, it should be appreciated that the invention may be implemented in many other forms without departing from the spirit or scope of the invention. For example, there are several references in the application to a "local device" communicating with a "remote device." It should be appreciated that the local device can refer to any device in the multi-site data sharing platform 100 (e.g., a patient telemedicine device 104, a specialist telemedicine device 108/110). The remote device refers to any other device that is connected with the local device through the cloud and/or a network and that is also in the multi-site data sharing platform 100 (e.g., a patient telemedicine device 104, a specialist telemedicine device 108/110, etc.). Various block diagrams have been presented in this application. However, it should be appreciated that the features and operations of one component in the diagram may be transferred to another component. Additionally, each component may be divided into multiple separate components or and/or merged with one or more other components. Some figures, such as FIGS. 2 and 3, include multiple components, inputs and data streams. It should be noted that in some implementations, fewer or more components, inputs and data streams may be involved. For example, FIG. 2 illustrates a patient telemedicine device 104 that receives simultaneous data streams from a probe 106*b*, a biometric waveform data source 106*c* and a biometric imaging source 106*d*. However, this application also contemplates embodiments in which, for example, biometric data is received from the probe and probe platform (e.g., an ultrasound probe), video is received from the video camera (e.g., video footage of the application and use of the probe on the body of a patient) and no biometric waveform data source and/or biometric imaging source is used.

In this application, there are references to a "telemedicine device" or "workstation" (e.g., a specialist telemedicine device, a patient telemedicine device, etc.) In some of the figures, the telemedicine device is depicted as having particular functions. For example, the patient telemedicine device is depicted as receiving data from multiple components and sources. However, it should be appreciated that the patient telemedicine device is not necessarily a single structure and in various embodiments is a system that includes multiple connected components that provide additional features or functionality. For example, the patient telemedicine device can incorporate or include additional adapters, connectors, modules, devices and/or any component described in the telemedicine system 102. In some embodiments, the patient telemedicine device incorporates an image acquisition device 202, a microphone 208, a video camera 106*a*, a diagnostic device, etc.) Therefore, the present embodiments should be considered illustrative and not restrictive and the invention is not to be limited to the details given herein.

What is claimed is:

1. A method for sharing medical data in a telemedicine session comprising:
   receiving a biometric imaging stream in real time from a medical scanning device at a first telemedicine device that is at a first location on a network;
   receiving a data stream in real time at a second telemedicine device that is at a second location on the network that is different from the first location, the data stream being one selected from the group consisting of a video stream received from a video camera and a biometric data stream that is received from a medical sensing device wherein the biometric imaging stream and the data stream are received simultaneously;
   obtaining a plurality of biometric imaging frames from the biometric imaging stream as the biometric imaging stream is being received;
   obtaining a plurality of data frames from the data stream as the data stream is being received;
   inserting timestamps into the biometric imaging and data frames so that they can be rendered synchronously in real time on a remote device;
   inserting a first timestamp into one of the biometric imaging frames at the first telemedicine device wherein the first timestamp is obtained at the first telemedicine device using a timing source selected from the group consisting of an NTP server and a GPS satellite;
   inserting a second timestamp into one of the data frames at the second telemedicine device wherein the second timestamp is obtained at the second telemedicine device using a timing source selected from the group consisting of an NTP server and a GPS satellite wherein the one of the biometric imaging frames is obtained at the first telemedicine device at approximately the same time as the one of the data frames is obtained at the second telemedicine device, thereby causing the first timestamp to be approximately the same as the second timestamp and helping to ensure that the ones of the biometric imaging and data frames are rendered approximately simultaneously at the remote device; and
   transmitting the biometric imaging and data frames in real time to the remote device while the biometric imaging and data streams are being received so that the biometric imaging and data frames can be rendered in substantially real time at the remote device.

2. A method as recited in claim 1 wherein:
   the biometric imaging stream is received from a medical scanning device that is being applied to a patient; and
   the video stream is received from a video camera that is directed a person using the second telemedicine device.

3. A method as recited in claim 1 further comprising:
   receiving the biometric imaging and data frames at the remote device; and
   rendering the biometric imaging and data frames in an order based on the timestamps.

4. A method as recited in claim 1, the method further comprising:
   partially encrypting the biometric imaging and data frames such that at least a portion of one or more of the frames is not encrypted.

5. A method as recited in claim 4 further comprising:
   the encrypting involves at least one selected from the group consisting of (1) encrypting a particular type of frame and not encrypting another type of frame; (2) encrypting a part of a frame and leaving other parts of the frame; (3) encrypting at least a portion of a header of a frame; (4) encrypting a portion of a header of a frame and a portion of media payload in the frame while leaving other parts of the frame unencrypted; and (5) encrypting only a header and not a media payload of the frame.

6. A method as recited in claim 4 further comprising:
   transmitting a message to the remote device indicating which part of each frame is encrypted.

7. A method as recited in claim 1 further comprising:
   compressing the biometric imaging stream at a first level of compression; and
   compressing the video stream at a second level of compression wherein the first level of compression is substantially less than the second level of compression.

8. A method as recited in claim 1 wherein:
   the biometric imaging stream is generated by at least one selected from the group consisting of an ultrasound device, an magnetic resonance imaging (MRI) device, a computed tomography (CT) device and an X-ray device.

9. A method as recited in claim 1 further comprising:
   receiving from a user an annotation on a particular biometric imaging frame;
   generating an annotation frame from the annotation;
   adding an annotation timestamp to the annotation frame and the biometric imaging frame so that when the annotation and biometric imaging frames are reconstructed and rendered at a rendering device, the annotation and the biometric imaging frames are synchronized; and
   transmitting the annotation frame and the biometric imaging frame to the rendering device.

10. A method as recited in claim 1 wherein:
    the biometric imaging stream is an ultrasound image stream that is generated using an ultrasound probe and that is received in real time; and
    the data stream is a video stream that is received in real time from a video camera.

11. A method as recited in claim 1, further comprising:
    receiving the biometric imaging frames in real time at the remote device over the network;
    receiving the data frames at the remote device over the network wherein the biometric imaging frames and the data frames are received simultaneously as they are being generated and transmitted;
    obtaining timestamps from the biometric imaging and data frames;
    synchronizing the biometric imaging and data frames based on the timestamps; and
    rendering the synchronized biometric imaging and data frames synchronously in real time as the biometric imaging and video frames are received over the network.

12. A method as recited in claim 11 wherein the synchronized frames are rendered in order based on the timestamps.

13. A method as recited in claim 11 further comprising:
    receiving from a user an annotation on a particular biometric imaging frame;
    generating an annotation frame from the annotation;
    associating the annotation frame and the biometric imaging frame with an annotation timestamp;
    inserting the annotation timestamp into the annotation frame and the biometric imaging frame so that when the biometric imaging frame and the annotation frame are rendered at a rendering device, the annotation and the biometric imaging frame are synchronized; and
    transmitting the biometric imaging and annotation frames to the rendering device.

14. A method as recited in claim 11 wherein:
the medical scanning device is at least one selected from the group consisting of an ultrasound device, a magnetic resonance imaging (MRI) device, a computed tomography (CT) device and an X-ray device.

15. A method as recited in claim 1 further comprising:
selectively encrypting a portion of the biometric imaging frames and leaving another portion of the biometric imaging frames unencrypted.

16. A method as recited in claim 15 wherein:
the selective encryption involves at least one selected from the group consisting of: (1) encrypting a particular type of frame and not encrypting another type of frame; (2) encrypting a part of each frame and leaving other parts of the frame unencrypted; (3) encrypting at least a portion of a header of each frame; (4) encrypting a portion of a header of each frame and a portion of media payload of the frame while leaving other parts of the frame unencrypted; and (5) encrypting only a header of each frame and not a media payload of the frame.

17. A method as recited in claim 15 further comprising:
receiving a second data stream from a second medical sensing device at the first location;
obtaining a plurality of second data stream data frames from the second data stream;
selectively encrypting a portion of the second data stream data frames and leaving another portion of the second data stream data frames unencrypted; and
transmitting the second data stream data frames to the remote device wherein:
the second data stream involves multichannel data obtained from the second medical sensing device;
the second medical sensing device is at least one selected from the group consisting of an electrocardiogram device, electroencephalography device, a pulse oximeter device, a thermal/temperature sensor, a blood pressure testing device, a glucose level testing device, and a pulmonary function testing device; and
the selective encryption of the second data stream data frames involves encrypting control information in a header of each second data stream data frame and leaving other parts of the frame unencrypted and wherein the control information indicates at least one selected from the group consisting of channel ID and sampling speed.

18. A method as recited in claim 15 wherein:
the selective encryption of the biometric imaging frames involves encrypting control information in a header of each biometric imaging frame and leaving other parts of the frame unencrypted and wherein the control information indicates at least one selected from the group consisting of (1) number of macroblocks in a portion of the frame; (2) a quantization table; and (3) DC coefficient of each of a plurality of macroblocks in the frame.

19. A telemedicine system comprising:
A first telemedicine device at a first location on a network, the first telemedicine device comprising:
a first processor; and
a first memory that stores computer readable instructions, which when executed by the first processor causes the first telemedicine device to:
receive a biometric imaging stream in real time from a medical scanning device;
obtain a plurality of biometric imaging frames from the biometric imaging stream as the biometric imaging stream is being received;
insert timestamps into the biometric imaging frames so that they can be rendered synchronously in real time on a remote device;
insert a first timestamp into one of the biometric imaging frames wherein the first timestamp is obtained at the first telemedicine device using a timing source selected from the group consisting of an NTP server and a GPS satellite; and
transmit the biometric imaging frames in real time to the remote device while the biometric imaging stream is being received so that the biometric imaging frames can be rendered in substantially real time at the remote device; and
A second telemedicine device at a second location on the network, the second telemedicine device comprising:
a second processor; and
a second memory that stores computer readable instructions, which when executed by the second processor causes the second telemedicine device to:
receive a data stream in real time, the data stream being one selected from the group consisting of a video stream received from a video camera and a biometric data stream that is received from a medical sensing device;
obtain a plurality of data frames from the data stream as the data stream is being received;
insert timestamps into the data frames so that they can be rendered synchronously in real time on the remote device;
insert a second timestamp into one of the data frames wherein the second timestamp is obtained at the second telemedicine device using a timing source selected from the group consisting of an NTP server and a GPS satellite and wherein the one of the biometric imaging frames is obtained at the first telemedicine device at approximately the same time as the one of the data frames is obtained at the second telemedicine device, thereby causing the first timestamp to be approximately the same as the second timestamp and helping to ensure that the ones of the biometric imaging and data frames are rendered simultaneously at the remote device; and
transmit the data frames in real time to the remote device while the data stream is being received so that the data frames can be rendered in substantially real time at the remote device.

20. A method as recited in claim 9 where the rendering device is one selected from the group consisting of the first telemedicine device, the second telemedicine device and the remote device.

* * * * *